US011049593B2

(12) United States Patent
 Kanada

(10) Patent No.: US 11,049,593 B2
(45) Date of Patent: Jun. 29, 2021

(54) MEDICAL EXAMINATION ASSISTANCE APPARATUS, OPERATION METHOD AND OPERATION PROGRAM THEREOF, AND MEDICAL EXAMINATION ASSISTANCE SYSTEM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 837 days.

(21) Appl. No.: 15/726,364

(22) Filed: Oct. 5, 2017

(65) Prior Publication Data
US 2018/0040088 A1 Feb. 8, 2018

Related U.S. Application Data

(63) Continuation of application No. PCT/JP2016/055497, filed on Feb. 24, 2016.

(30) Foreign Application Priority Data

Apr. 7, 2015 (JP) ............................. JP2015-078193

(51) Int. Cl.
*G16H 10/60* (2018.01)
*G06Q 10/10* (2012.01)
(Continued)

(52) U.S. Cl.
CPC ............ *G16H 10/60* (2018.01); *G06Q 10/103* (2013.01); *G16H 15/00* (2018.01); *G16H 50/70* (2018.01); *G16H 40/20* (2018.01); *Y02A 90/10* (2018.01)

(58) Field of Classification Search
CPC ........ G16H 50/20; G16H 10/60; G16H 50/30; G16H 50/70; G16H 50/50; G16H 15/00;
(Continued)

(56) References Cited

U.S. PATENT DOCUMENTS

2004/0172225 A1* 9/2004 Hochberg .............. G16H 50/30
703/2
2012/0054230 A1 3/2012 Kanada
(Continued)

FOREIGN PATENT DOCUMENTS

JP 2007279942 10/2007
JP 2012048395 3/2012
(Continued)

OTHER PUBLICATIONS

"International Search Report (Form PCT/ISA/210) of PCT/JP2016/055497", dated Mar. 29, 2016, with English translation thereof, pp. 1-5.
(Continued)

*Primary Examiner* — Joseph D Burgess
(74) *Attorney, Agent, or Firm* — JCIPRNET

(57) ABSTRACT

An acquisition unit 47 acquires comparative cases, which are medical examination data having the same clinical path as a medical examination target patient, from an electronic medical record DB 14. A display form determination unit 48 compares the treatment periods and the conditions of respective comparative cases, and assigns each comparative case to each group. A display color is set in advance for each group. A screen display control unit 49 generates a graph comparison display screen 21 on which a line graph 70 showing a time-series change in the examination value of the medical examination target patient and a plurality of line graphs 71 showing time-series changes in the examination values of respective comparative cases are displayed so as to overlap each other. The line graph 71 is color-coded with display colors determined by the display form determination unit 48.

22 Claims, 28 Drawing Sheets

(51) Int. Cl.
*G16H 50/70* (2018.01)
*G16H 15/00* (2018.01)
*G16H 40/20* (2018.01)

(58) Field of Classification Search
CPC ........ G16H 10/20; G16H 10/40; G06Q 50/24;
G06Q 50/22; G06F 19/00; G06F 19/325;
G06F 19/3418
See application file for complete search history.

(56) References Cited

U.S. PATENT DOCUMENTS

| | | | |
|---|---|---|---|
| 2012/0116180 A1* | 5/2012 | Rothman | G16H 50/70 600/300 |
| 2012/0262472 A1* | 10/2012 | Garr | G06T 11/206 345/589 |
| 2014/0095202 A1* | 4/2014 | Kudou | G16H 10/20 705/3 |
| 2014/0275819 A1 | 9/2014 | Kassem et al. | |
| 2015/0254430 A1 | 9/2015 | Oosawa et al. | |

FOREIGN PATENT DOCUMENTS

| | | |
|---|---|---|
| JP | 2014109836 | 6/2014 |
| JP | 2014179091 | 9/2014 |
| WO | 2014084294 | 6/2014 |

OTHER PUBLICATIONS

"Written Opinion of the International Searching Authority (Form PCT/ISA/237)" of PCT/JP2016/055497, dated Mar. 29, 2016, with English translation thereof, pp. 1-10.

Office Action of China Counterpart Application, with English translation thereof, dated Sep. 18, 2020, pp. 1-23.

Office Action of China Counterpart Application, with English translation thereof, dated Apr. 14, 2021, pp. 1-23.

* cited by examiner

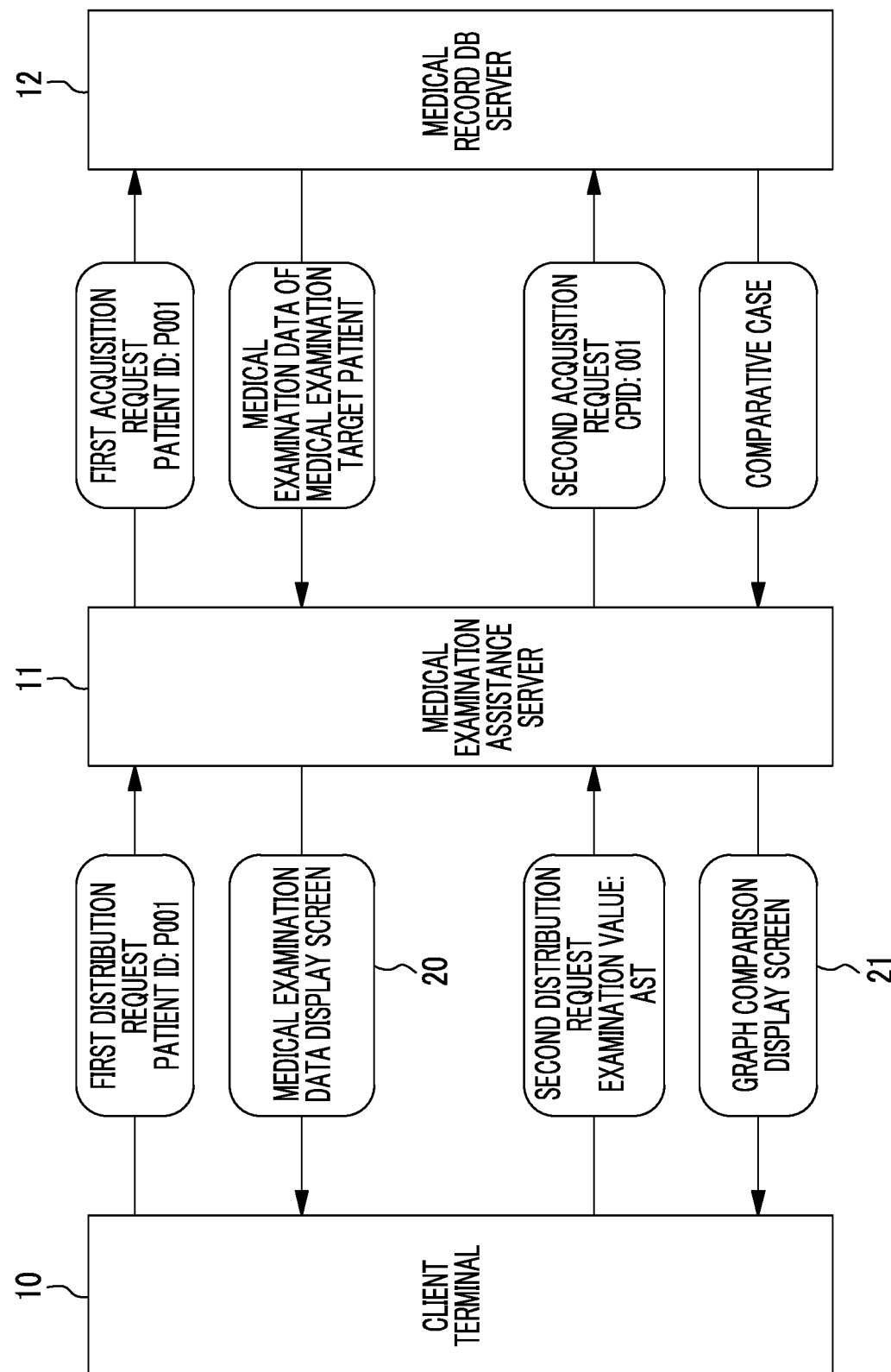

FIG. 3

| DATE | BLOOD PRESSURE (MAXIMUM) | DATE AND BLOOD PRESSURE TIME (MINIMUM) | | DATE | BODY TEMPERATURE |
|---|---|---|---|---|---|
| 02.02.2015 | 196 | 07/22/2014 | 92 | 02.02.2015 | 38.9 |
| 02.03.2015 | 180 | 07/23/2014 | 84 | 02.03.2015 | 37.6 |
| 02.04.2015 | 175 | 07/24/2014 | 79 | 02.04.2015 | 36.9 |

| DATE | BIOCHEMICAL EXAMINATION | DATE | BLOOD TEST |
|---|---|---|---|
| 02.02.2015 | AST/49 ALP/452 CREATININE/1.4··· | 02.02.2015 | WBC/2.63 RBC/9.25 Ht/58.8 ALB/4.9··· |
| 02.03.2015 | AST/41 ALP/395 CREATININE/1.1··· | 02.03.2015 | WBC/3.77 RBC/7.63 Ht/52.4 ALB/4.9··· |
| 02.04.2015 | AST/36 ALP/323 CREATININE/0.8··· | 02.04.2015 | WBC/4.12 RBC/5.67 Ht/51.1 ALB/4.7··· |

| DATE | THERAPEUTIC DRUG A | DATE | MEDICAL EXAMINATION AND TREATMENT RECORD |
|---|---|---|---|
| 02.02.2015 | 100 | 02.02.2015 | CHIEF COMPLAINT: ABDOMINAL PAIN, NAUSEA<br>ORDER OF MEDICAL EXAMINATIONS: BIOCHEMISTRY, BLOOD, SIMPLE X-RAY IMAGING, AND ENDOSCOPIC EXAMINATION<br>DIAGNOSED DISEASE NAME: ACUTE GASTRIC ULCER<br>ADMISSION TO HOSPITAL CPID: CP001 ADMINISTRATION: THERAPEUTIC DRUG A |
| 02.03.2015 | 100 | 02.03.2015 | ORDER OF MEDICAL EXAMINATIONS: BIOCHEMISTRY, BLOOD, SIMPLE X-RAY IMAGING ADMINISTRATION: THERAPEUTIC DRUG A SURGERY ORDER, EXPLANATION |
| 02.04.2015 | 50 | 02.04.2015 | ORDER OF MEDICAL EXAMINATIONS: BIOCHEMISTRY, BLOOD ABROSIA: MORNING, NOON<br>SURGERY: ENDOSCOPIC MUCOSAL RESECTION |

···

14

| PATIENT ID | ELECTRONIC MEDICAL RECORD |
|---|---|
| P001 | |

| PATIENT ID | ELECTRONIC MEDICAL RECORD |
|---|---|
| P002 | |

| PATIENT ID | ELECTRONIC MEDICAL RECORD |
|---|---|
| P003 | |

| DISEASE TYPE | DISEASE NAME | THERAPEUTIC DRUG |
|---|---|---|
| STANDARD PNEUMONIA | PNEUMOCOCCAL PNEUMONIA | PENICILLIN TYPE A, B, C, ···, CEPHEM TYPE A, B, C, ··· |
| | KLEBSIELLA PNEUMONIA PNEUMONIA | PENICILLIN TYPE A, B, C, ···, CEPHEM TYPE A, B, C, ··· |
| | STAPHYLOCOCCUS AUREUS PNEUMONIA | METHICILLON X, Y, Z, VANCOMYCIN X, Y, Z |
| ATYPICAL PNEUMONIA | PSEUDOMONAS AERUGINOSA PNEUMONIA | STREPTOMYCIN L, M, N, ··· |
| | MYCOPLASMA PNEUMONIA | MACROLIDE TYPE P, Q, R, ···, TETRACYCLINE TYPE P, Q, R, ··· |
| | CHLAMYDIA PNEUMONIA | MACROLIDE TYPE P, Q, R, ···, TETRACYCLINE TYPE P, Q, R, ··· |

130

MEDICAL EXAMINATION ASSISTANCE APPARATUS, OPERATION METHOD AND OPERATION PROGRAM THEREOF, AND MEDICAL EXAMINATION ASSISTANCE SYSTEM

CROSS-REFERENCE TO RELATED APPLICATIONS

This application is a Continuation of PCT International Application No. PCT/JP2016/055497 filed on Feb. 24, 2016, which claims priority under 35 U.S.C § 119(a) to Patent Application No. 2015-078193 filed in Japan on Apr. 7, 2015, all of which are hereby expressly incorporated by reference into the present application.

BACKGROUND OF THE INVENTION

1. Field of the Invention

The present invention relates to a medical examination assistance apparatus, an operation method and non-transitory computer readable recording medium storing an operation program thereof, and a medical examination assistance system.

2. Description of the Related Art

In medical facilities, introduction of electronic medical records for digitizing and managing various kinds of medical examination data acquired in the course of medical examination for patients is under progress. The medical examination data includes: examination values (measurement values) of vital signs of patients; examination values of various medical examinations including subject examinations, such as biochemical examinations and blood tests, or physiological examinations, such as electroencephalographic examinations; and medical examination and/or treatment records in which types and doses of therapeutic drugs, the contents of medical examinations, the contents of treatment, disease names, order of various medical examinations, and events, such as admission and discharge that occurred in the course of medical examination for patients, are recorded. These various kinds of medical examination data are registered in the electronic medical record in time series together with the dates of acquisition dates, such as measurement dates, examination dates, administration dates, and medical examination dates.

In a medical facility that has introduced the electronic medical record, it is possible to provide various kinds of information for assisting diagnosis to a doctor in the form of electronic data. For example, JP2014-109836A discloses a medical examination assistance apparatus that provides a graph, which shows a time-series change in the examination value of a medical examination target patient, so that the degree of progress of the disease of the medical examination target patient is grasped or the treatment effect after the surgery for the medical examination target patient or after the administration of therapeutic drug is determined.

In JP2014-109836A, in order to make it possible to compare and study the medical condition of the medical examination target patient and the medical condition of another patient, a graph showing a time-series change in the examination value of a comparative case, which is the medical examination data of a patient having the same disease name as the medical examination target patient, is displayed in parallel with the graph of the examination value of the medical examination target patient, or these graphs are displayed so as to overlap each other.

SUMMARY OF THE INVENTION

For the doctor, it is very important to predict the future medical condition of the medical examination target patient with reference to the examination value. In particular, in a case where it is predicted that the medical condition will become worse at the early stage of treatment, it is possible to perform appropriate treatment for the medical examination target patient earlier. Then, since the treatment outcome is improved eventually, the prediction of the future medical condition is also very important for the medical examination target patient.

In JP2014-109836A, the graph of the examination value of the comparative case is displayed in parallel with the graph of the examination value of the medical examination target patient, or these graphs are displayed so as to overlap each other. However, since it is not known whether the treatment outcome of the comparative case is good or bad, it is difficult to predict the future medical condition only with the display. Therefore, in the current situation, the future medical condition of the medical examination target patient is predicted empirically by the doctor.

Thus, in the current situation where the prediction of the future medical condition depends on the experience of a doctor, an inexperienced doctor overlooks the sign of disease deterioration. For this reason, there is a risk of adverse effects such as prolonged treatment. Therefore, a mechanism capable of easily predicting the future medical condition of the medical examination target patient without being influenced by the doctor's experience has been requested.

It is an object of the present invention to provide a medical examination assistance apparatus capable of easily predicting the future medical condition of a medical examination target patient, an operation method and non-transitory computer readable recording medium storing an operation program thereof, and a medical examination assistance system.

In order to achieve the aforementioned object, a medical examination assistance apparatus of the present invention comprises: an acquisition unit that acquires, from a case database in which medical examination data including examination values registered in time series is registered for each patient, the medical examination data of a medical examination target patient and a plurality of comparative cases that are the medical examination data of comparison targets; a display form determination unit that determines a display form, which is for displaying the plurality of comparative cases so as to be distinguished from each other, according to treatment outcomes of the comparative cases; and a screen display control unit that performs control to display a medical examination target patient graph showing a time-series change in each of the examination values of the medical examination target patient and comparative case result information indicating the treatment outcome of each of the comparative cases on a display screen so as to overlap each other and that generates the comparative case result information according to the display form determined by the display form determination unit.

It is preferable that the display form determination unit determines the display form for each of the comparative cases and that the screen display control unit generates a comparative case graph showing a time-series change in the examination value of each of the comparative cases, as the comparative case result information, for each of the comparative cases and distinguishes the plurality of comparative case graphs according to the display form. In this case, it is preferable that the comparative case graph is shown by a line graph connecting the examination values of each of the comparative cases to each other using lines for each acquisition date of the examination value. Alternatively, it is preferable that the comparative case graph is shown by points obtained by plotting the examination values of each of the comparative cases for each acquisition date of the examination value.

It is preferable that a reference date for displaying the medical examination target patient graph and the comparative case graph so as to overlap each other is set along a time axis.

Alternatively, it is preferable that a two-dimensional region having two axes of the examination value and an acquisition date of the examination value is set on the display screen, the display form determination unit sets a plurality of rectangular regions by dividing the two-dimensional region in units of the examination value and units of the acquisition date and determines the display form according to the treatment outcome of the comparative case, in which the examination value is present within the rectangular region, for the plurality of rectangular regions, and the screen display control unit generates a heat map, in which the rectangular regions are distinguished according to the display form, as the comparative case result information.

It is preferable that the display form determination unit calculates an index value of the treatment outcome of the comparative case in which the examination value is present within the rectangular region and determines the display form according to the calculated index value. It is preferable that the index value is an average value of the treatment outcomes. Alternatively, it is preferable that the index value is a ratio between the number of comparative cases with good treatment outcomes and the number of comparative cases with poor treatment outcomes.

It is preferable that a distribution of the number of comparative cases is displayed on the heat map.

It is preferable that the medical examination data includes a clinical path that summarizes a treatment plan for a patient and that the comparative cases are the medical examination data having the same clinical path as the medical examination target patient. In the case of displaying the medical examination target patient graph and the comparative case graph so as to overlap each other along the time axis, it is preferable that an application start date of the clinical path is set as the reference date.

It is preferable that the medical examination data includes contents of surgery performed on a patient and that the comparative cases are the medical examination data having the same surgical contents as the medical examination target patient. In the case of displaying the medical examination target patient graph and the comparative case graph so as to overlap each other along the time axis, it is preferable that a date of the surgery is set as the reference date.

It is preferable that the medical examination data includes a disease name of a patient and a therapeutic drug administered to the patient and that the comparative cases are the medical examination data having the same disease name and therapeutic drug as the medical examination target patient. In the case of displaying the medical examination target patient graph and the comparative case graph so as to overlap each other along the time axis, it is preferable that an administration start date of the therapeutic drug is set as the reference date.

It is preferable that the display form determination unit determines the display form according to a length of a treatment period. Alternatively, it is preferable that the medical examination data includes a clinical path that summarizes a treatment plan for each patient and a variance that does not conform to the treatment plan and that the display form determination unit determines the display form according to the variance.

It is preferable that the display form determination unit determines a display color as the display form.

An operation method of a medical examination assistance apparatus of the present invention comprises: an acquisition step of acquiring, from a case database in which medical examination data including examination values registered in time series is registered for each patient, the medical examination data of a medical examination target patient and a plurality of comparative cases that are the medical examination data of comparison targets; a display form determination step of determining a display form, which is for displaying the plurality of comparative cases so as to be distinguished from each other, according to treatment outcomes of the comparative cases; and a screen display control step of performing control to display a medical examination target patient graph showing a time-series change in each of the examination values of the medical examination target patient and comparative case result information indicating the treatment outcome of each of the comparative cases on a display screen so as to overlap each other and of generating the comparative case result information according to the display form determined in the display form determination step.

A non-transitory computer readable recording medium storing an operation program of a medical examination assistance apparatus of the present invention causes a computer to execute: an acquisition function of acquiring, from a case database in which medical examination data including examination values registered in time series is registered for each patient, the medical examination data of a medical examination target patient and a plurality of comparative cases that are the medical examination data of comparison targets; a display form determination function of determining a display form, which is for displaying the plurality of comparative cases so as to be distinguished from each other, according to treatment outcomes of the comparative cases; and a screen display control function of performing control to display a medical examination target patient graph showing a time-series change in each of the examination values of the medical examination target patient and comparative case result information indicating the treatment outcome of each of the comparative cases on a display screen so as to overlap each other and of generating the comparative case result information according to the display form determined by the display form determination function.

A medical examination assistance system of the present invention is medical examination assistance system comprising a medical examination assistance apparatus, and comprises: an acquisition unit that acquires, from a case database in which medical examination data including examination values registered in time series is registered for each patient, the medical examination data of a medical examination target patient and a plurality of comparative cases that are the medical examination data of comparison targets; a display form determination unit that determines a display form, which is for displaying the plurality of comparative cases so as to be distinguished from each other, according to treatment outcomes of the comparative cases; and a screen display control unit that performs control to display a medical examination target patient graph showing a time-series change in each of the examination values of the medical examination target patient and comparative case result information indicating the treatment outcome of each of the comparative cases on a display screen so as to overlap each other and that generates the comparative case result information according to the display form determined by the display form determination unit.

According to the present invention, the medical examination data of the medical examination target patient and a plurality of comparative cases that are the medical examination data of comparison targets are acquired, a display form for displaying the plurality of comparative cases so as to be distinguished from each other is determined according to the treatment outcomes of the comparative cases, and the medical examination target patient graph showing a time-series change in each of the examination values of the medical examination target patient and the comparative case result information, which indicates the treatment outcome of each comparative case and is generated in the determined display form, are displayed on the display screen so as to overlap each other. Therefore, it is possible to provide a medical examination assistance apparatus capable of easily predicting the future medical condition of the medical examination target patient, an operation method and a non-transitory computer readable recording medium storing an operation program thereof, and a medical examination assistance system.

BRIEF DESCRIPTION OF THE DRAWINGS

FIG. 2 is a diagram showing various kinds of information transmitted and received between a client terminal, a medical examination assistance server, and a medical record DB server.

FIG. 3 is a diagram showing the contents of an electronic medical record DB.

FIG. 26 is a diagram showing a disease name and therapeutic drug table.

DESCRIPTION OF THE PREFERRED EMBODIMENTS

First Embodiment

Figure 1:
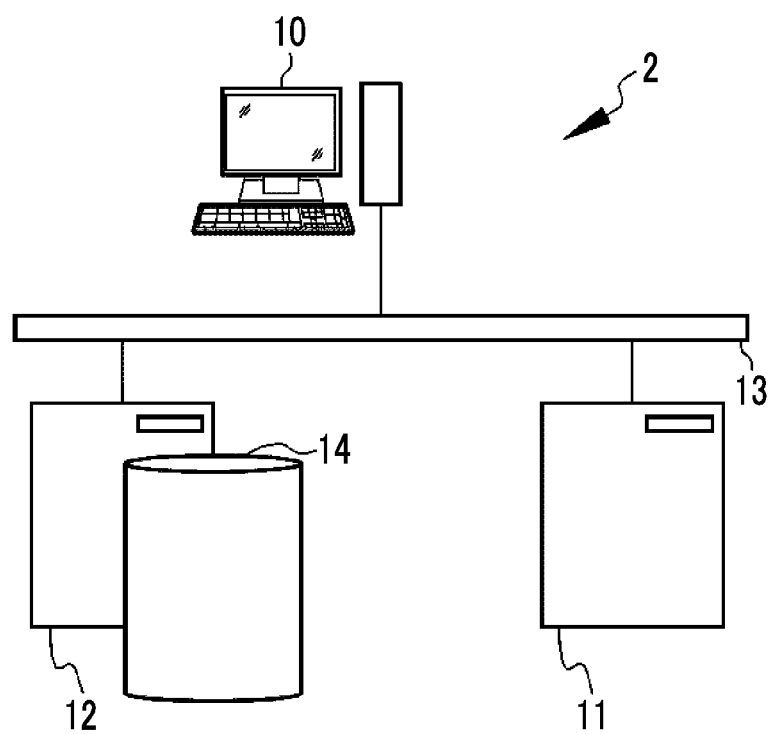
FIG. 1 is a diagram showing a medical examination assistance system.

In FIG. 1, a medical examination assistance system 2 includes a client terminal 10 and a medical examination assistance server 11 corresponding to a medical examination assistance apparatus. The client terminal 10 and the medical examination assistance server 11 are connected to each other through a network 13, such as a local area network (LAN) provided in the medical facility. A medical record database (hereinafter, abbreviated as a database (DB)) server 12 is also connected to the network 13.

Each of the client terminal 10, the medical examination assistance server 11, and the medical record DB server 12 is configured by installing a control program, such as an operating system, or various application programs on a computer as a base, such as a personal computer, a server computer, or a workstation.

The medical examination assistance server 11 has a diagnostic assistance information providing function for providing diagnostic assistance information for assisting patient diagnosis. The medical record DB server 12 has a medical record management function for managing electronic medical records.

The client terminal 10 is operated by a medical staff of a medical facility, such as a doctor who performs medical examination for a patient or a laboratory technician who performs a medical examination. The client terminal 10 is used in the case of performing medical examination for a patient using various functions of the medical examination assistance server 11 and the medical record DB server 12. Specifically, the client terminal 11 is used in the case of viewing diagnostic assistance information or electronic medical records or in the case of inputting various kinds of medical examination data in the electronic medical record (refer to FIG. 3). In FIG. 1, only one client terminal 10 is drawn. In practice, however, a plurality of client terminals 10 are provided for each medical department, such as internal medicine, surgery, examination department, and rehabilitation department, or each medical staff.

An electronic medical record DB 14 corresponding to a case database is provided in the medical record DB server 12. Electronic medical records are registered in the electronic medical record DB 14 so as to be searchable.

In FIG. 2, the client terminal 10 outputs a first distribution request and a second distribution request to the medical examination assistance server 11. The first distribution request includes patient identification data (ID) of the medical examination target patient who is an object of a medical examination. The patient ID is a symbol or a number for identifying an individual patient who visits a medical facility. In addition to the patient ID of the medical examination target patient, the second distribution request includes an item of examination value (only the item of examination value is shown in FIG. 2).

The medical examination assistance server 11 receives the first distribution request and the second distribution request from the client terminal 10. The medical examination assistance server 11 outputs a first acquisition request having the same contents as the first distribution request to the medical record DB server 12.

The medical examination assistance server 11 outputs the second acquisition request to the medical record DB server 12, for example, twice. The first-time second acquisition request includes a patient ID of the medical examination target patient. The second-time second acquisition request includes an ID (CPID) of a clinical path (hereinafter, abbreviated as a CP) adopted for the medical examination target patient (only the second-time second acquisition request is shown in FIG. 2).

The medical record DB server 12 receives the first acquisition request from the medical examination assistance server 11, searches for medical examination data associated with the patient ID included in the first acquisition request (hereinafter, referred to as medical examination data of the medical examination target patient), and outputs the medical examination data to the medical examination assistance server 11.

In addition, the medical record DB server 12 receives the second acquisition request from the medical examination assistance server 11, searches for medical examination data of the medical examination target patient in response to the first-time second acquisition request, searches for medical examination data (hereinafter, referred to as a comparative case) of a target to be compared with the medical examination target patient in response to the second-time second acquisition request, and outputs the pieces of medical examination data to the medical examination assistance server 11 (only the comparative case is shown in FIG. 2).

The medical examination assistance server 11 acquires the medical examination data of the medical examination target patient and the comparative case from the medical record DB server 12. The medical examination assistance server 11 generates a medical examination data display screen 20 (also refer to FIG. 14) based on the medical examination data of the medical examination target patient. In addition, the medical examination assistance server 11 generates a graph comparison display screen 21 (corresponding to a display screen; also refer to FIG. 15 or the like) as diagnostic assistance information based on the medical examination data of the medical examination target patient and the comparative case. The medical examination assistance server 11 outputs the generated display screens 20 and 21 to the client terminal 10 that is the output source of each distribution request.

The medical examination assistance server 11 outputs the display screens 20 and 21, for example, in the form of Extensible Markup Language (XML) data for web distribution that is generated by a markup language, such as the XML. The client terminal 10 reproduces and displays the display screens 20 and 21 on the web browser based on the XML data. Instead of the XML, other data description languages, such as JavaScript (registered trademark) Object Notation (JSON), may be used.

Although not shown, in addition to the first distribution request and the second distribution request, the client terminal 10 outputs an electronic medical record registration request and an electronic medical record distribution request to the medical record DB server 12. The medical record DB server 12 registers the electronic medical record received by the registration request in a retrievable form in the electronic medical record DB 14, and manages the electronic medical record. In addition, the medical record DB server 12 searches for the electronic medical record designated by the distribution request from the electronic medical record DB 14, and outputs the searched electronic medical record to the client terminal 10 that is the output source of the distribution request.

In FIG. 3, in the electronic medical record DB 14, an electronic medical record is registered for each patient so as to be associated with a patient ID. The electronic medical record registered in the electronic medical record DB 14 can be searched for based on the patient ID.

The electronic medical record includes various kinds of medical examination data. The medical examination data includes: examination values (measurement values) of vital signs, such as patient's blood pressure, body temperature, heartbeat, pulse, and oxygen saturation; examination values of various medical examinations including subject examinations, such as biochemical examinations and blood tests, or physiological examinations, such as electroencephalographic examinations; and medical examination and/or treatment records in which types and doses of therapeutic drugs, the contents of medical examinations, the contents of treatment, disease names, order of various medical examinations, and events, such as admission and discharge that occurred in the course of medical examination for patients, are recorded. These various kinds of medical examination data are registered in time series together with the dates of acquisition dates, such as measurement dates, examination dates, administration dates, and medical examination dates.

In FIG. 3, examination values of respective items of blood pressure (maximum), blood pressure (minimum), and body temperature are exemplified as examination values of vital signs. In addition, examination values of respective items, such as aspartate aminotransferase (AST), alkaline phosphatase (ALP), and creatinine of biochemical examinations, and examination values of respective items, such as white blood cell count (WBC), red blood cell count (RBC), hematocrit (Ht), and albumin (ALB) of blood test, are exemplified as examination values of medical examinations, and the dose of therapeutic drug A is exemplified as the type and dose of therapeutic drug. In addition, a chief complaint such as abdominal pain and nausea obtained by interview, acute gastric ulcer of diagnosed disease name, order of medical examinations such as biochemistry, blood, simple X-ray imaging, and endoscopic examination, CP001 that is the CPID of the adopted CP, and the like are recorded as examples of the medical examination and/or treatment records.

The CP is generated in advance for each disease type or each disease name in order to bring about an ideal treatment result for the medical examination target patient. The CP is a summary of a daily plan (treatment plan) of various treatments or the like to be performed for the medical examination target patient, such as medical examinations, surgery, rehabilitation, and meals. The medical staff performs treatment or the like along the treatment plan indicated by the CP. In a case where variance, which is treatment or the like that does not conform to the treatment plan indicated by the CP, occurs, the contents of the variance is recorded in the medical examination and/or treatment records by the medical staff (refer to FIG. 19).

The CPID is a symbol or a number for identifying each CP. The same CPID is assigned to CPs whose treatment plans generated for each disease type or disease name are the same.

As the medical examination data, in addition to the above examples, health management information measured on a daily basis by a patient using simple test equipment such as a blood pressure measuring instrument or a weighing scale in a home or genetic test information as a result of patient's genetic test may be included.

Figure 4:
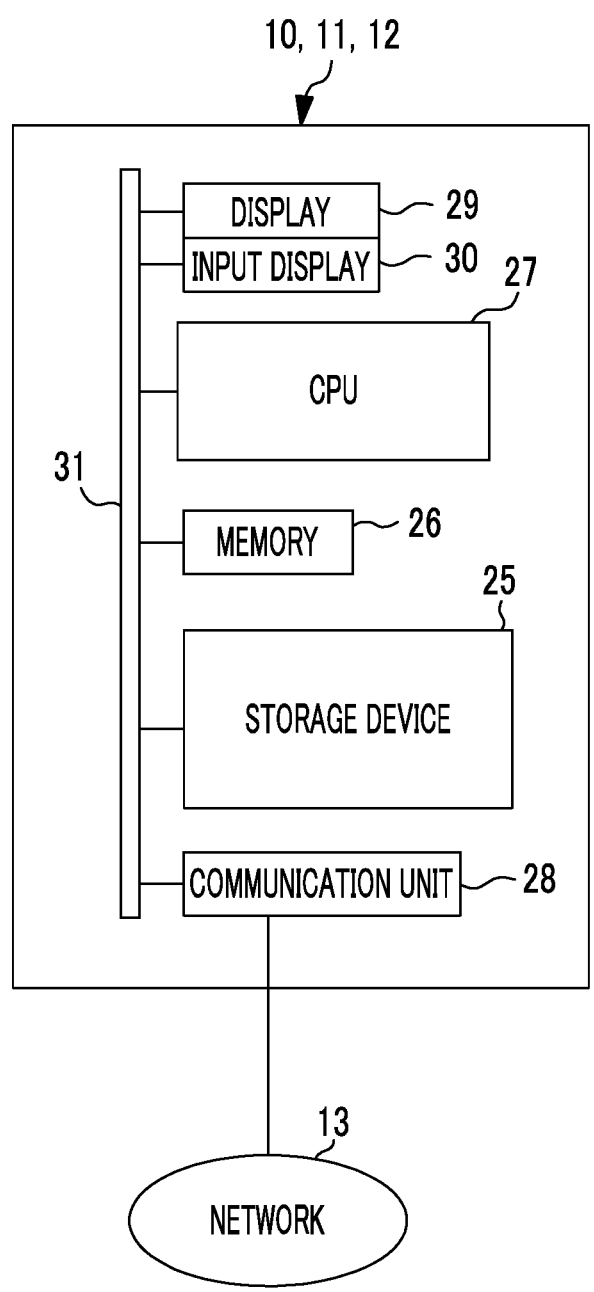
FIG. 4 is a block diagram showing a computer that forms a client terminal, a medical examination assistance server, and a medical record DB server.

In FIG. 4, the basic configurations of computers that form the client terminal 10, the medical examination assistance server 11, and the medical record DB server 12 are the same, and each computer includes a storage device 25, a memory 26, a central processing unit (CPU) 27, a communication unit 28, a display 29, and an input device 30. These are connected to each other through a data bus 31.

The storage device 25 is a hard disk drive, which is built into a computer that forms the client terminal 10 or the like or which is connected to the computer through a cable or a network, or a disk array formed by connecting a plurality of hard disk drives. Control programs such as an operating system, various application programs, and display data of various operation screens associated with these programs are stored in the storage device 25.

The memory 26 is a work memory required in a case where the CPU 27 executes processing. The CPU 27 performs overall control of each unit of the computer by loading a program stored in the storage device 25 to the memory 26 and executing the processing according to the program.

The communication unit 28 is a network interface to perform transmission control of various kinds of information through the network 13. The display 29 displays various operation screens corresponding to the operation of the input device 30, such as a mouse or a keyboard. The operation screen has an operation function based on the graphical user interface (GUI). Each computer that forms the client terminal 10 or the like receives an input of an operation instruction from the input device 30 through the operation screen.

In the following explanation, for the sake of distinction, a suffix "A" is attached to the reference numeral of each unit of the computer that forms the client terminal 10, a suffix "B" is attached to the reference numeral of each unit of the computer that forms the medical examination assistance server 11, and a suffix "C" is attached to the reference numeral of each unit of the computer that forms the medical record DB server 12.

Figure 5:
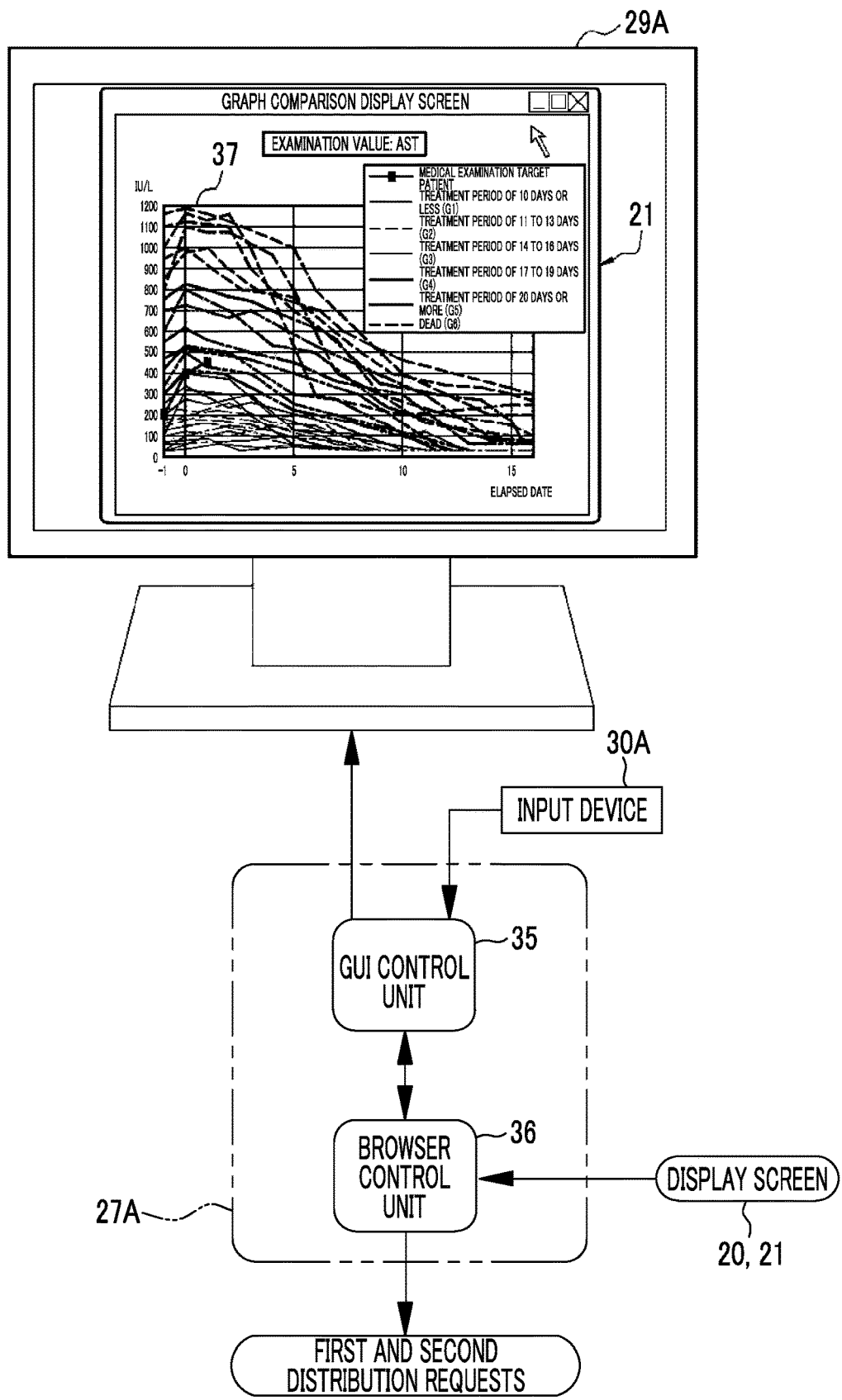
FIG. 5 is a block diagram showing the function of a CPU of a client terminal.

In FIG. 5, in a case where a web browser is started, the CPU 27A of the client terminal 10 cooperates with the memory 26 to function as a GUI control unit 35 and a browser control unit 36.

The GUI control unit 35 displays various operation screens on the display 29A, and receives an operation instruction that is input from the input device 30A through various operation screens. Operation instructions include an instruction to distribute the medical examination data display screen 20, specifically, an instruction to input the patient ID of the medical examination target patient, and an instruction to distribute the graph comparison display screen 21, specifically, an instruction to input an item of the examination value. The GUI control unit 35 outputs the received patient ID of the medical examination target patient and the received item of the examination value to the browser control unit 36.

The browser control unit 36 controls the operation of the web browser. The browser control unit 36 issues a first distribution request, which includes the patient ID of the medical examination target patient from the GUI control unit 35, and a second distribution request, which includes the item of the examination value from the GUI control unit 35, to the medical examination assistance server 11.

The browser control unit 36 receives XML data of each of the display screens 20 and 21 from the medical examination assistance server 11. The browser control unit 36 reproduces the display screens 20 and 21 to be displayed on the web browser based on the XML data, and outputs the display screens 20 and 21 to the GUI control unit 35. The GUI control unit 35 displays the display screens 20 and 21 on the display 29A.

FIG. 5 shows a state in which the graph comparison display screen 21 is displayed on the display 29A. A graph display region 37 is provided on the graph comparison display screen 21.

Figure 6:
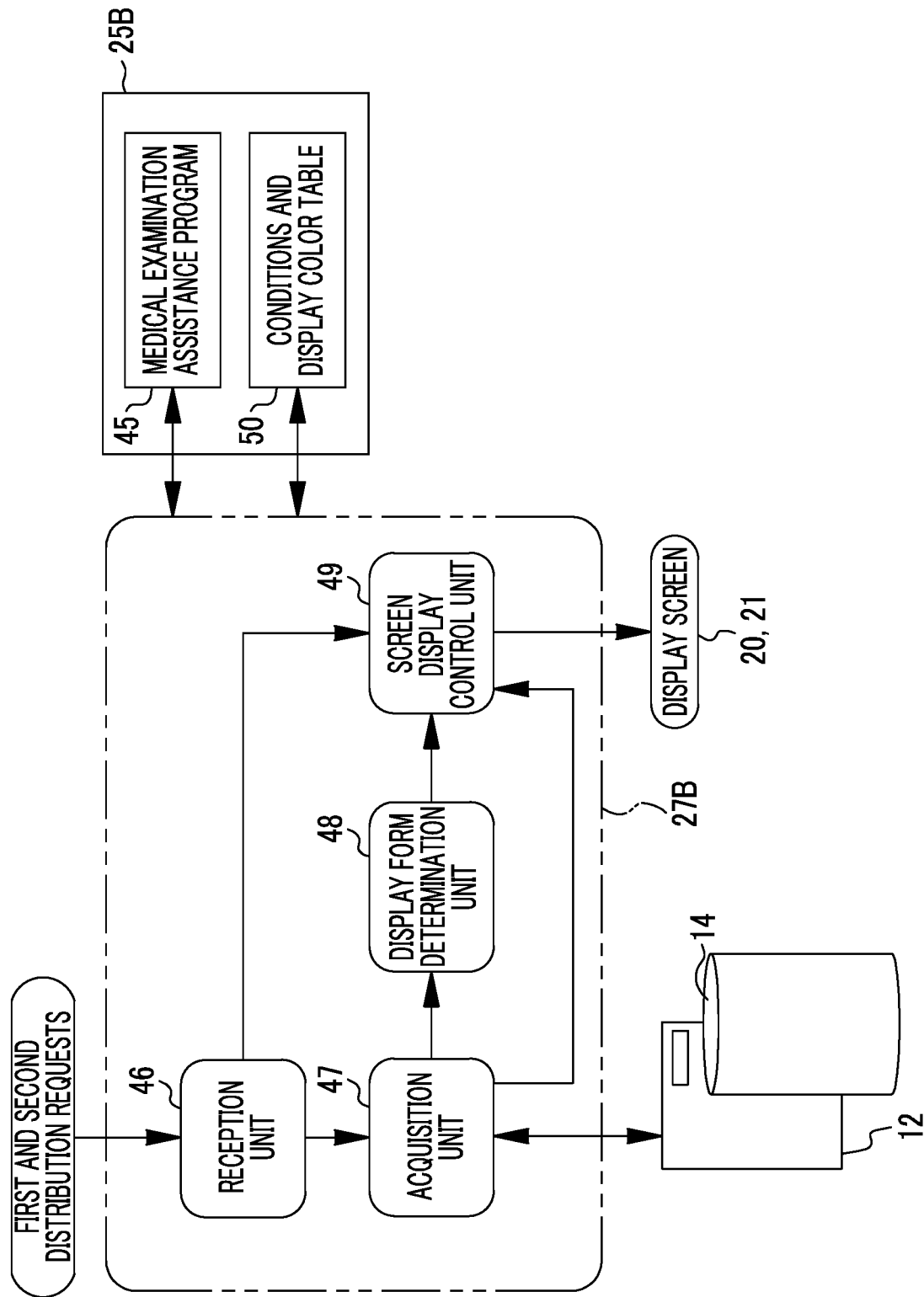
FIG. 6 is a block diagram showing the function of a CPU of a medical examination assistance server.

In FIG. 6, a medical examination assistance program 45 is stored in a storage device 25B of the medical examination assistance server 11. The medical examination assistance program 45 is an application program for operating a computer, which forms the medical examination assistance server 11, as a medical examination assistance apparatus, and corresponds to an operation program.

In a case where the medical examination assistance program 45 is started, the CPU 27B of the medical examination assistance server 11 cooperates with the memory 26 to function as a reception unit 46, an acquisition unit 47, a display form determination unit 48, and a screen display control unit 49.

The reception unit 46 receives the first distribution request and the second distribution request from the client terminal 10. The reception unit 46 outputs the patient ID of the medical examination target patient, which is included in the first distribution request and the second distribution request, to the acquisition unit 47. The reception unit 46 outputs the item of the examination value included in the second distribution request to the screen display control unit 49.

The acquisition unit 47 issues a first acquisition request, which includes the patient ID of the medical examination target patient, and a second acquisition request, which includes the patient ID of the medical examination target patient and the CPID of the medical examination target patient, to the medical record DB server 12.

The acquisition unit 47 acquires the medical examination data of the medical examination target patient and the comparative case that are output from the medical record DB server 12 in response to the first acquisition request and the second acquisition request. The acquisition unit 47 outputs the medical examination data of the medical examination target patient and the comparative case to the screen display control unit 49, and outputs the comparative case to the display form determination unit 48.

The display form determination unit 48 determines a display color as a display form for displaying a plurality of comparative cases so as to be distinguished from each other. More specifically, the display form determination unit 48 determines display colors, which are for displaying time-series changes in the examination values of a plurality of comparative cases from the acquisition unit 47 by color coding, based on a conditions and display color table 50 (also refer to FIG. 10) stored in the storage device 25B (refer to FIG. 11). The display form determination unit 48 determines a display color for each comparative case according to the treatment outcome of the comparative case. The display form determination unit 48 outputs display color designation information 66 (refer to FIG. 11), which is a display color determination result, to the screen display control unit 49.

The screen display control unit 49 generates the medical examination data display screen 20 based on the medical examination data of the medical examination target patient from the acquisition unit 47. With reference to the display color designation information 66 from the display form determination unit 48, the screen display control unit 49 generates the graph comparison display screen 21 based on the medical examination data of the medical examination target patient and the comparative case from the acquisition unit 47 (refer to FIGS. 12 and 13). The screen display control unit 49 outputs the XML data of the generated display screens 20 and 21 to the client terminal 10 that is the output source of each distribution request.

Figure 7:
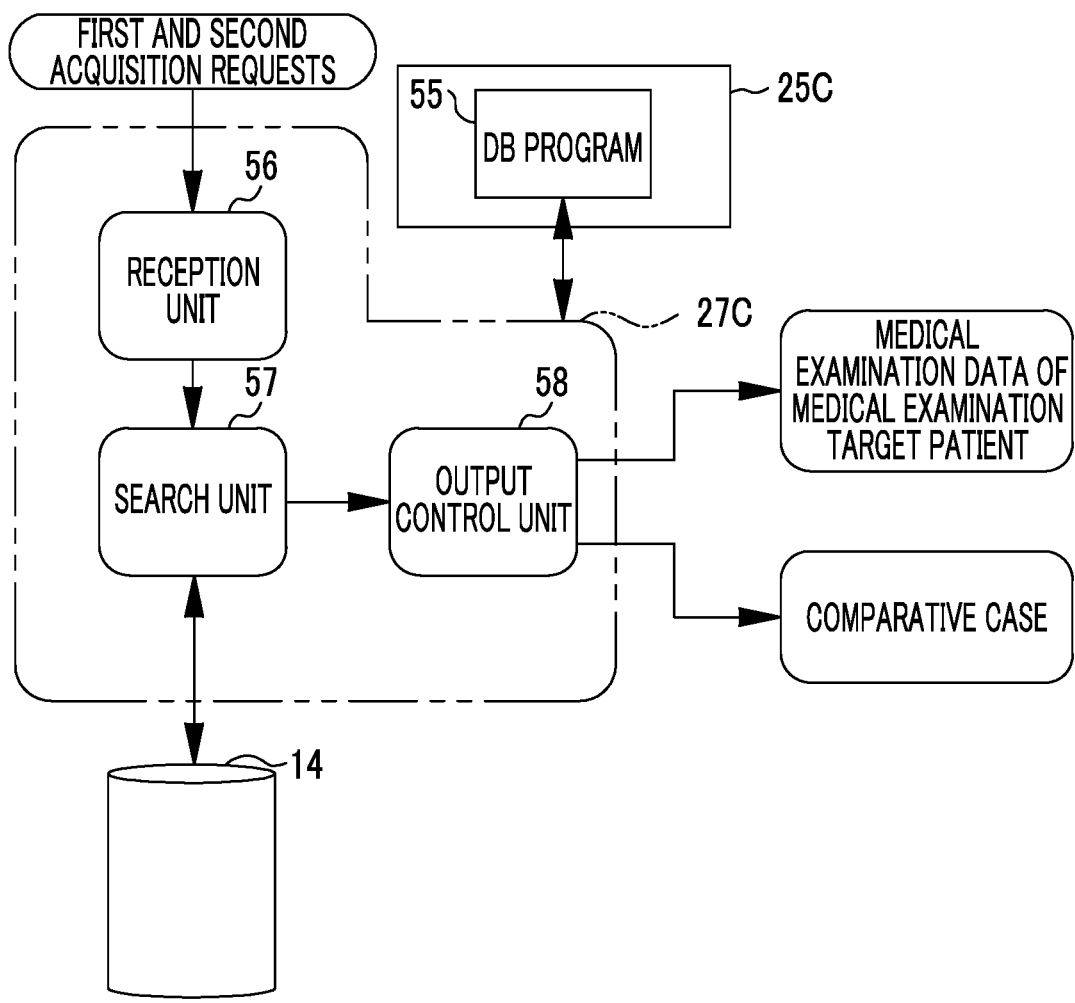
FIG. 7 is a block diagram showing the function of a CPU of a medical record DB server.

In FIG. 7, a DB program 55 is stored in the storage device 25C of the medical record DB server 12. In a case where the DB program 55 is started, the CPU 27C of the medical record DB server 12 cooperates with the memory 26 to function as a reception unit 56, a search unit 57, and an output control unit 58.

The reception unit 56 receives the first acquisition request and the second acquisition request from the medical examination assistance server 11. The reception unit 56 outputs to the search unit 57 the patient ID of the medical examination target patient included in the first acquisition request, the patient ID of the medical examination target patient included in the first-time second acquisition request, and the CPID of the medical examination target patient included in the second-time second acquisition request.

The search unit 57 searches for the medical examination data of the medical examination target patient from the electronic medical record DB 14 in response to the first acquisition request and the first-time second acquisition request, and searches for a comparative case in response to the second-time second acquisition request. The search unit 57 outputs the medical examination data of the medical examination target patient and the comparative case, which have been searched for, to the output control unit 58. The output control unit 58 outputs the medical examination data of the medical examination target patient and the comparative case to the medical examination assistance server 11.

Although not shown, the reception unit 56 also receives a request for registration of the electronic medical record and a request for distribution of the electronic medical record. The search unit 57 searches for the electronic medical record from the electronic medical record DB 14 in response to the request for distribution of the electronic medical record. In addition, the search unit 57 also has a registration function for registering the electronic medical record in the electronic medical record DB 14 in response to the request for registration of the electronic medical record. The output control unit 58 outputs the electronic medical record, which has been searched by the search unit 57, to the client terminal 10 that is the output source of the distribution request.

Figure 8:
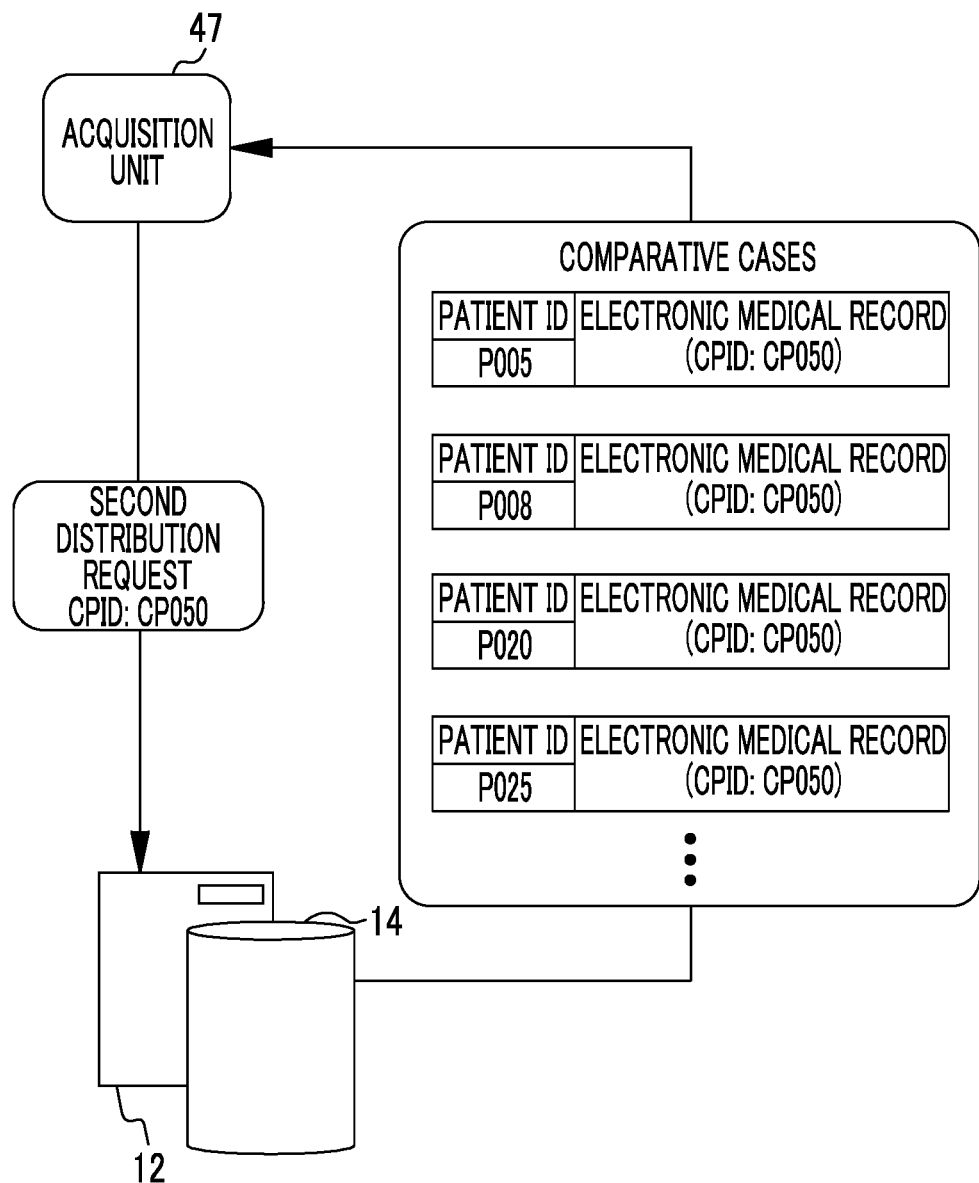
FIG. 8 is a diagram illustrating the acquisition function of an acquisition unit.

The acquisition unit 47 acquires medical examination data, which has the same clinical path (CP) as the medical examination target patient, as a comparative case. For example, in FIG. 8, in a case where the CPID "CP050" is recorded in the medical examination and/or treatment records of the electronic medical record of the medical examination target patient, the acquisition unit 47 outputs the second-time second acquisition request including the CPID "CP050" to the medical record DB server 12. In the medical record DB server 12, the search unit 57 searches for the medical examination data of the electronic medical record of patients (patients with patient IDs "P005", "P008", and the like) in which the CPID "CP050" is recorded in the medical examination and/or treatment records, as a comparative case, from the electronic medical record of each patient of the electronic medical record DB 14. As a result, the acquisition unit 47 acquires, medical examination data of the electronic medical record of a patient, in which the same CPID "CP050" as the medical examination target patient is recorded in the medical examination and/or treatment records, as a comparative case.

Figure 9:
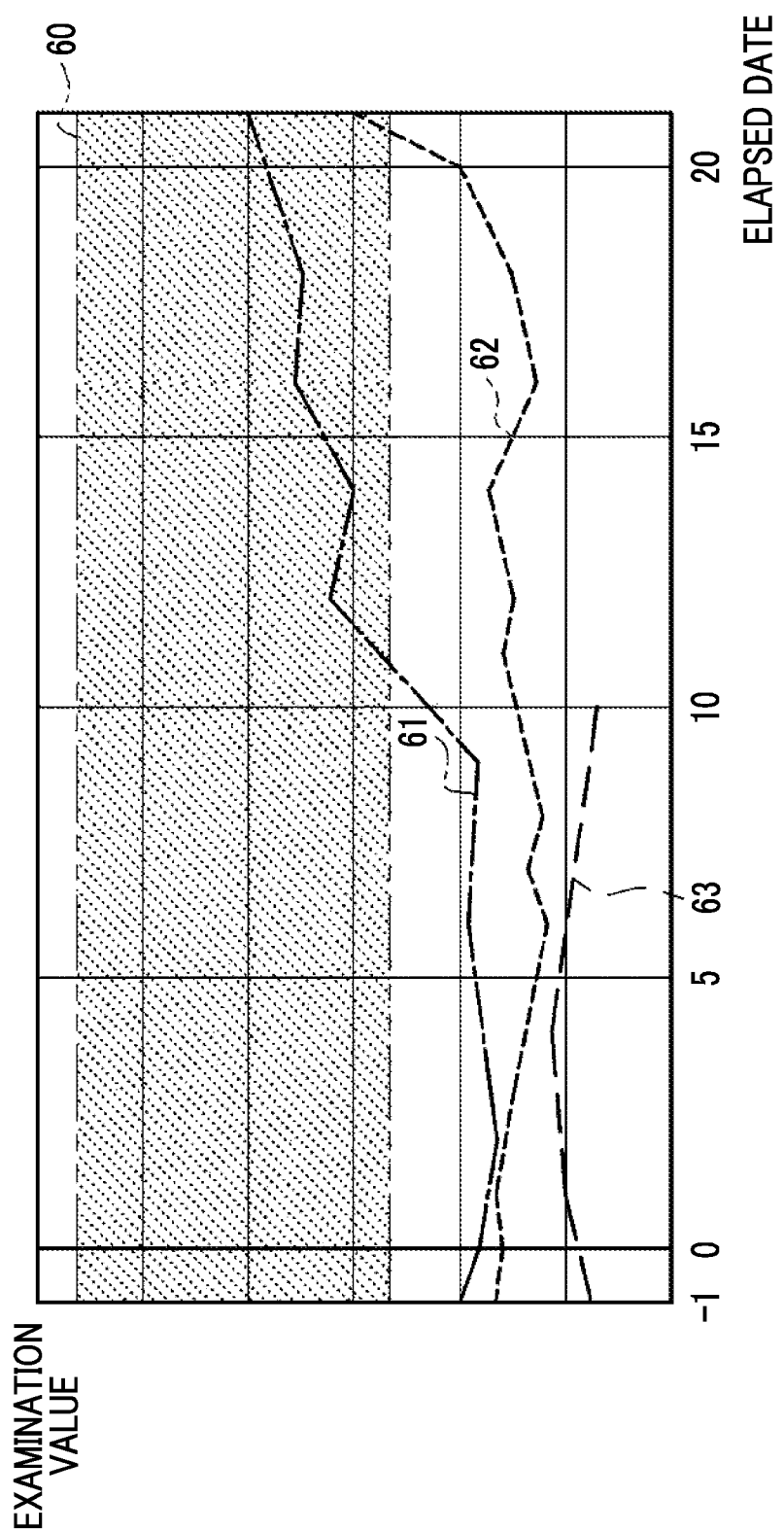
FIG. 9 is a graph showing a time-series change in the examination value of a certain item.

FIG. 9 is a graph showing a time-series change in the examination value of a certain item. The examination value is assigned to the vertical axis, and the elapsed date is assigned to the horizontal axis. The elapsed date "0" is the treatment start date of the medical examination target patient. Reference numeral 60 indicated by hatching and two-dot chain line shows the normal range of the examination value of the item.

In a line graph 61 indicated by the one-dot chain line, the examination value is within the normal range 60 on the elapsed date "11", and the examination value remains within the normal range 60 after the elapsed date "11". On the other hand, in a line graph 62 indicated by the narrow broken line, the examination value fall within the normal range 60 on the elapsed date "21". A line graph 63 indicated by the wide broken line is discontinued after the elapsed date "10" since the patient died on the elapsed date "10".

Here, it is assumed that a patient of a comparative case whose time-series change in the examination value is indicated by the line graph 61 was discharged on, for example, the elapsed date "12", and the patient of a comparative case whose time-series change in the examination value is indicated by the line graph 62 was discharged after, for example, the elapsed date "21". In this case, since the treatment period in the comparative case whose time-series change in the examination value is indicated by the line graph 61 is relatively shorter than that in the comparative case whose time-series change in the examination value is indicated by the line graph 62, it can be said that the treatment outcome in the comparative case whose time-series change in the examination value is indicated by the line graph 61 is better than that in the comparative case whose time-series change in the examination value is indicated by the line graph 62.

Conversely, it can be said that the treatment outcome in the comparative case whose time-series change in the examination value is indicated by the line graph 62 is worse than that in the comparative case whose time-series change in the examination value is indicated by the line graph 61. In the comparative case whose time-series change in the examination value is indicated by the line graph 63, it can be said that the treatment outcome is bad since the patient is dead.

Thus, the treatment outcome is determined depending on the length of the treatment period and whether the patient is alive or dead. Therefore, in the present embodiment, the display form determination unit 48 determines a display color according to the length of the treatment period and whether the patient is alive or dead.

Figure 10:
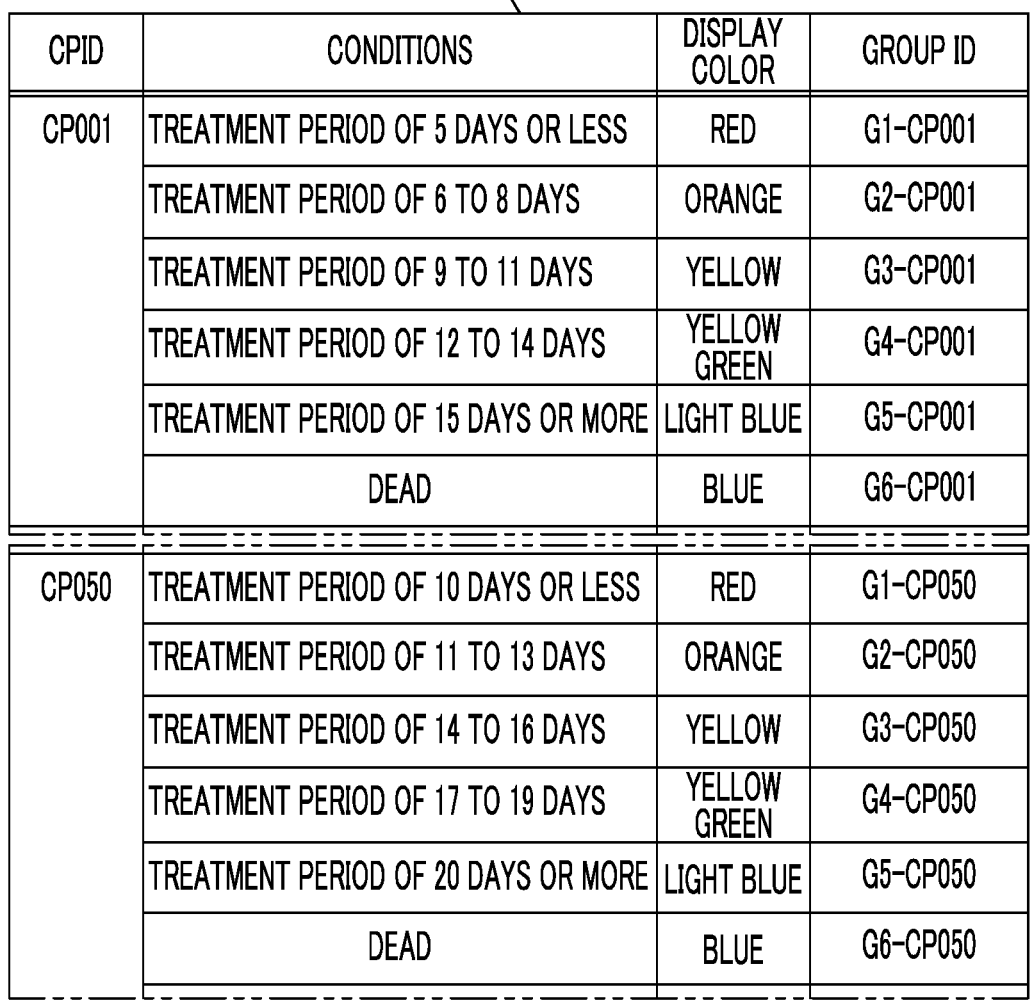
FIG. 10 is a diagram showing the contents of a conditions and display color table.

In FIG. 10, in the conditions and display color table 50, conditions, display colors, and group IDs are set in advance for each CPID. The length of the treatment period and whether the patient is alive or dead, such as "treatment period of 5 days or less", "treatment period of 17 to 19 days", and "dead", are registered as conditions. "Red", "orange", "blue", and the like are registered as display colors. The group ID is a symbol or a number for identifying a group of comparative cases assigned under each condition.

Conditions relevant to the treatment period are set based on the standard treatment period defined by the CP or the average treatment period for each disease type or disease name announced by a public institution. In these cases, as exemplified in FIG. 10, conditions relevant to the treatment period are different for each CP, disease type or disease name. Needless to say, the conditions relevant to the treatment period may be set uniformly regardless of the CP or the disease type or the disease name.

Figure 11:
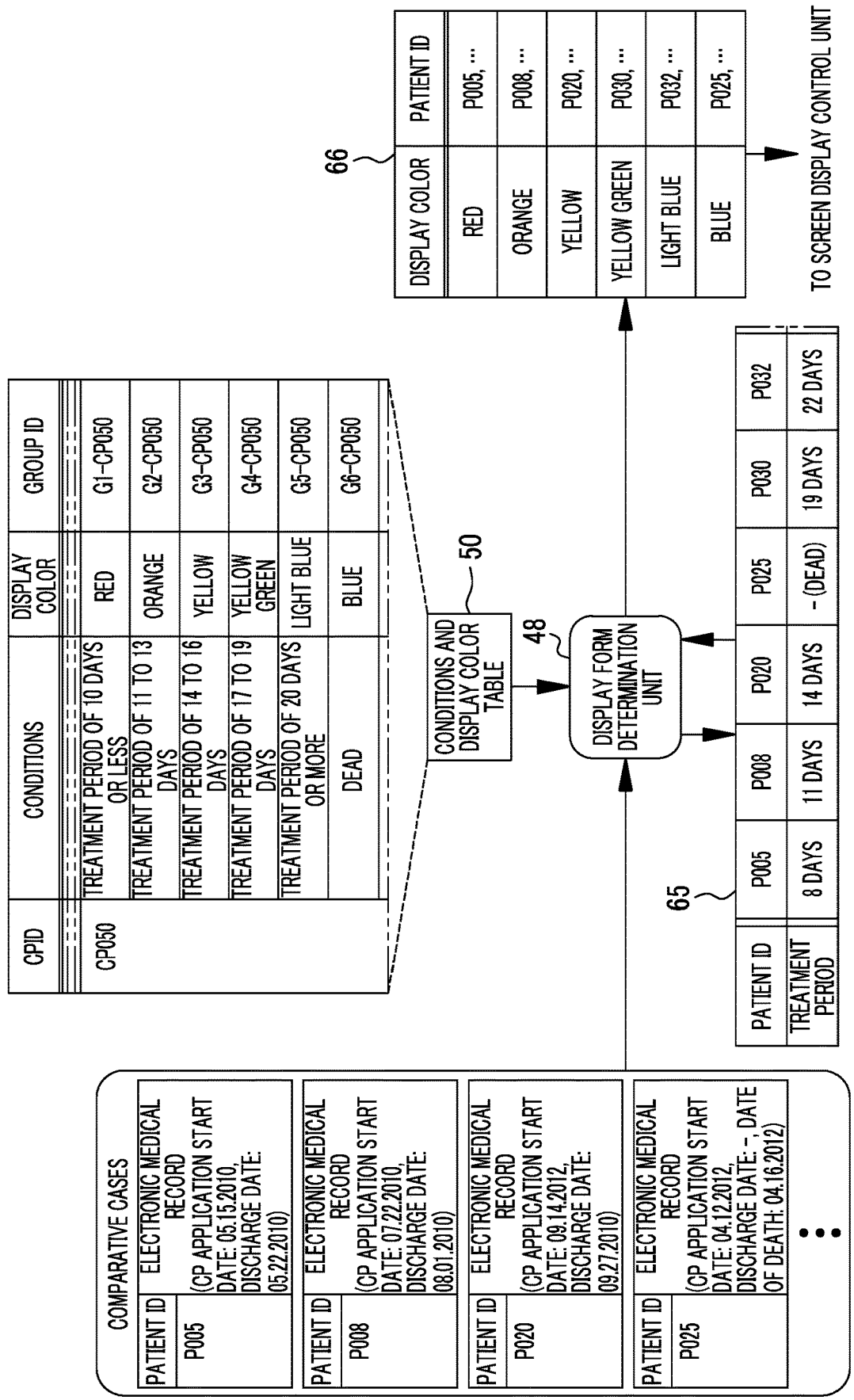
FIG. 11 is a diagram illustrating the display form determination function of a display form determination unit.

In FIG. 11, the display form determination unit 48 generates intermediate processing data 65 first. The intermediate processing data 65 is obtained by calculating the treatment period with the CP application start date recorded in the medical examination and/or treatment records as the start date of the treatment period and the discharge date as the end date of the treatment period and associating the calculated treatment period with the patient ID of the comparative case for each comparative case from the acquisition unit 47.

For example, in the case of a comparative case of patient ID "P005", since the CP application start date recorded in the medical examination and/or treatment records is "2010. 05. 15" and the discharge date is "2010. 05. 22", "eight days" is calculated as the treatment period. In a case where the patient is dead as in the comparative case of patient ID "P025", the display form determination unit 48 does not calculate the treatment period. The treatment period may be calculated with the discharge date as the end date of the treatment period as described above, or the treatment period may be calculated with the day before the discharge date as the end date of the treatment period. Instead of the discharge date, the administration end date of therapeutic drug may be used as the end date of the treatment period. The start date and the end date of the treatment period are not limited to the CP application start date, the discharge date or the date before the discharge date, and the administration end date of therapeutic drug. For example, the start date and the end date of the treatment period may be any date, such as the start date and the end date of treatment manually input based on the determination of the medical staff. In any case, for the setting of the start date and the end date of the treatment period, the same criteria are applied between the medical examination data of the medical examination target patient and the comparative case.

The display form determination unit 48 compares the treatment period of the intermediate processing data 65 with the conditions in the conditions and display color table 50, and assigns each comparative case to a group corresponding to each condition. The display form determination unit 48 generates the display color designation information 66 that summarizes the allocation result of comparative cases. In the display color designation information 66, the patient ID of the comparative case assigned to each group is written so as to correspond to the display color. For example, since the treatment period of the comparative case of patient ID "P005" is "eight days", the patient ID "P005" is written in the display color "red" in a case where the conditions are "treatment period of 10 days or less". In addition, since a patient with patient ID "P025" is dead, the patient ID "P025" is written in the display color "blue" in a case where the conditions are "dead".

Figure 12:
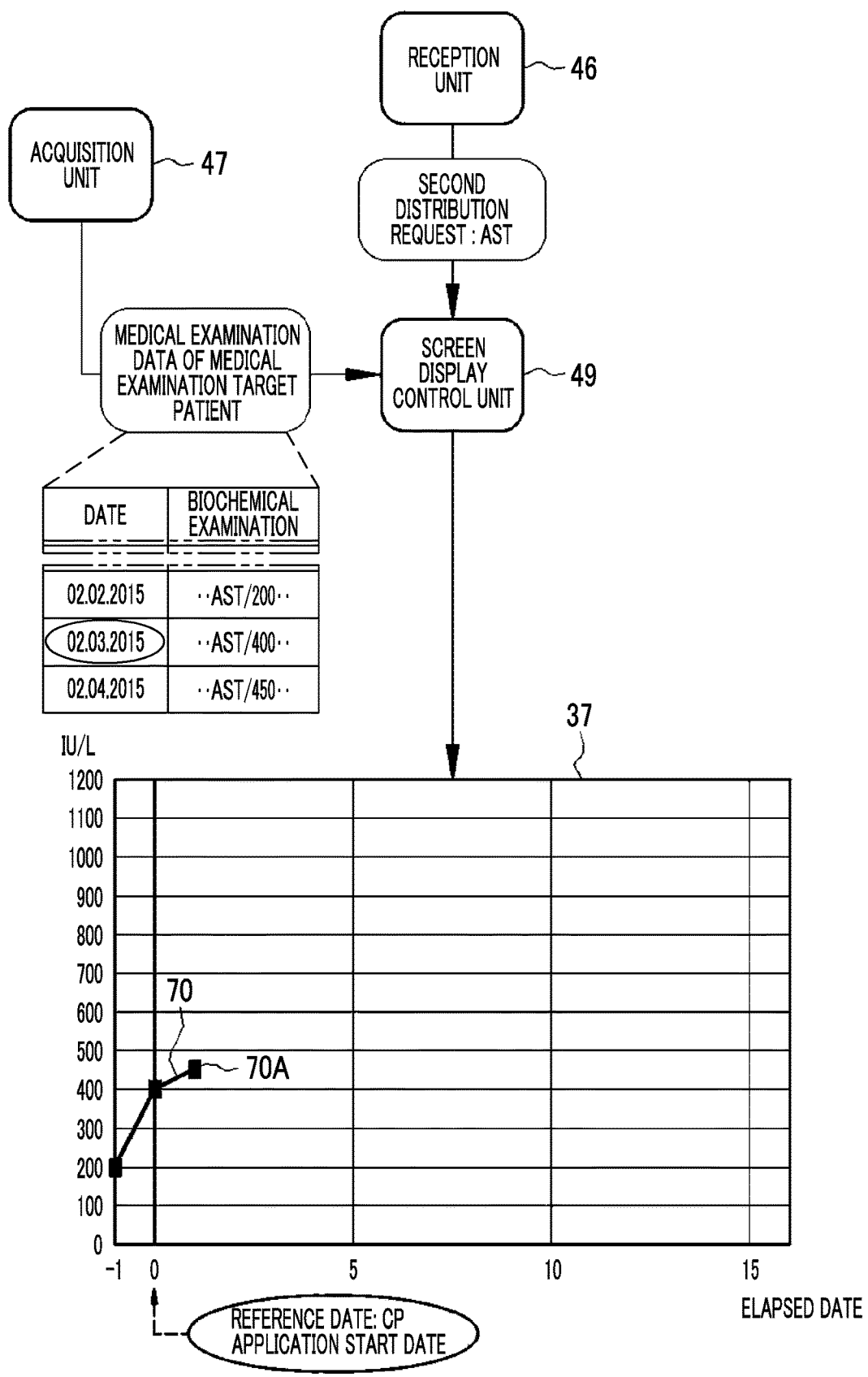
FIG. 12 is an explanatory diagram conceptually showing the processing of generating a line graph, which shows a time-series change in the examination value of a medical examination target patient, by a screen display control unit.

In FIG. 12, for example, in a case where a second distribution request in which the AST is specified in the item of the examination value is received from the reception unit 46, the screen display control unit 49 generates a line graph 70, which shows a time-series change in the AST examination value of the medical examination target patient indicated by the solid line and square points 70A, in the graph display region 37 based on the medical examination data of the medical examination target patient from the acquisition unit 47. The line graph 70 corresponds to a medical examination target patient graph. Since the examination value is assigned to the vertical axis and the elapsed date (date of acquisition of the examination value) from the reference date is assigned to the horizontal axis, the graph display region 37 corresponds to a two-dimensional region.

The screen display control unit 49 sets the CP application start date as the elapsed date "0", that is, the reference date. In FIG. 12, "2015. 02. 03" surrounded by the solid ellipse is the CP application start date. Therefore, an AST examination value "400" on the CP application start date "2015. 02. 03" is plotted on the acquisition date "0". In addition, an AST examination value "200" on the previous day "2015. 02. 02" is plotted on the acquisition date "−1", and an AST examination value "450" on the next day "2015. 02. 04" is plotted on the acquisition date "1". The line graph 70 is obtained by connecting the AST examination values of the medical examination target patient, which are plotted as described above, to each other using the line.

Figure 13:
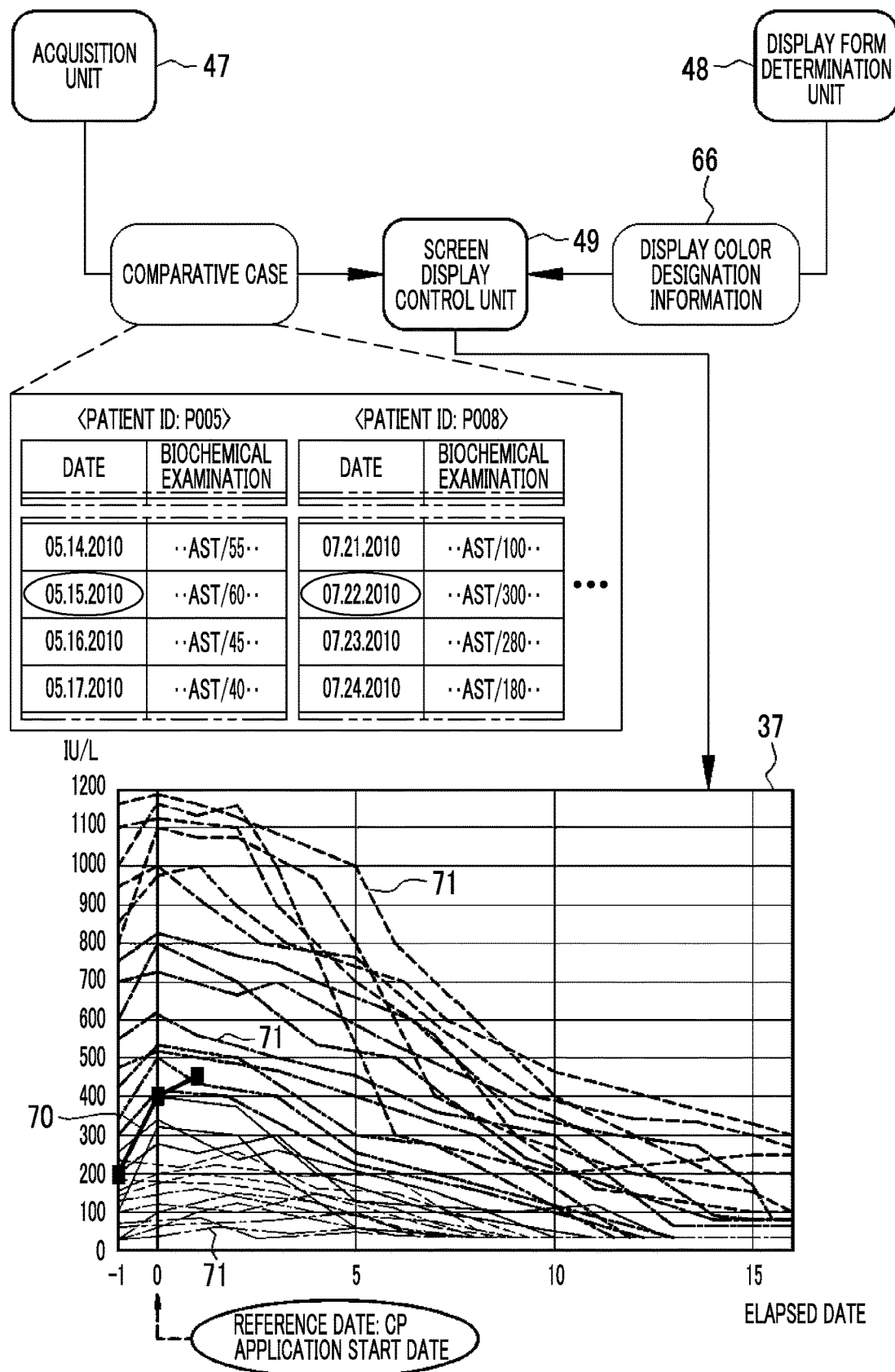
FIG. 13 is an explanatory diagram conceptually showing the processing of generating line graphs, which show time-series changes in the examination values of comparative cases, by the screen display control unit.

In FIG. 13, the screen display control unit 49 generates a plurality of line graphs 71 showing time-series changes in the AST examination values of a plurality of comparative cases, as comparative case result information, in the graph display region 37 based on a plurality of comparative cases from the acquisition unit 47. The plurality of line graphs 71 correspond to comparative case graphs.

The screen display control unit 49 color-codes the plurality of line graphs 71 with display colors based on the display color designation information 66 from the display form determination unit 48. For example, in the case of the line graph 71 of the AST examination value of the comparative case of patient ID "P005", from the display color designation information 66 in FIG. 11, the display color "red" is assigned to the patient ID "P005". Therefore, it can be seen that red is preferable as the display color of the line graph 71 of the AST examination value of the comparative case of patient ID "P005".

As in the case of generating the line graph 70, the screen display control unit 49 also sets the CP application start date as a reference date in the case of generating the line graph 71. In FIG. 13, "2010. 05. 15", "2010. 07. 22", and the like surrounded by the solid ellipses are CP application start dates.

By generating the line graph 70 and the line graph 71 in the graph display region 37 as described above by the screen display control unit 49, the line graph 70 and the line graph 71 are eventually displayed so as to overlap each other in the graph display region 37. Although it has been described herein that the line graph 71 is generated after generating the line graph 70, there is no particular order in generating the graphs 70 and 71.

Figure 14:
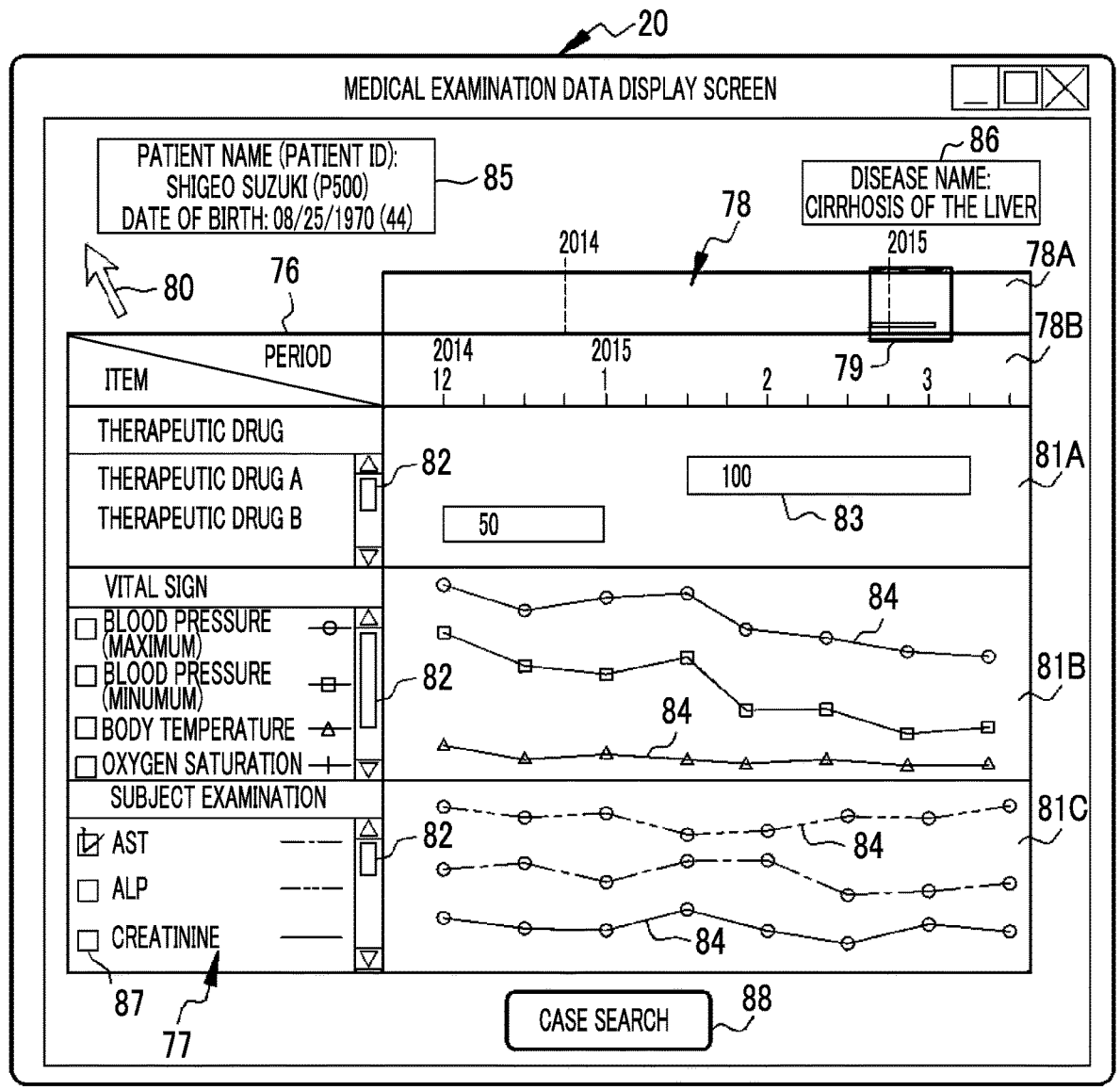
FIG. 14 is a diagram showing a medical examination data display screen.

In FIG. 14, the medical examination data display screen 20 has a medical examination data display region 76. A display field 77 of major category names of medical examination data, such as therapeutic drug, vital signs, and subject examinations, and names of individual items of medical examination data, such as therapeutic drug A, blood pressure (maximum), body temperature, and AST, is disposed on the vertical axis of the medical examination data display region 76. A display field 78 of the acquisition period of medical examination data displayed in the medical examination data display region 76 is disposed on the horizontal axis of the medical examination data display region 76.

The display field 78 is divided into a first display field 78A and a second display field 78B. The time scale of a period expressed in the first display field 78A (referred to as a first period) is relatively longer than that of a period expressed in the second display field 78B (referred to as a second period).

A period indicator 79 is provided in the first display field 78A. The period indicator 79 shows to which part of the first period the second period corresponds. The width of the period indicator 79 corresponds to the width of the second period in the time scale of the first period. In FIG. 14, since the second period is about three and a half months from December, 2014 to mid-March, 2015, the width of the period indicator 79 corresponds to the width of about three and a half months in the time scale of the first period.

By moving the period indicator 79 in the horizontal direction with a cursor 80 or by changing the width of the period indicator 79, it is possible to change the display range of the second period. The second period to be first displayed on the medical examination data display screen 20 may be a period before a predetermined period from the latest medical examination data, or may be designated by the medical staff in the case of inputting the patient ID of the medical examination target patient by distribution instruction on the initial screen on the web browser.

The medical examination data display region 76 is divided into a plurality of sub-regions 81A, 81B, and 81C for each major category of medical examination data. Therapeutic drug, vital signs, and subject examinations are assigned to the sub-regions 81A, 81B, and 81C, respectively. A scroll bar 82 for displaying a non-display item by vertical scroll operation is provided in the display field 77 of the sub-regions 81A to 81C.

In the sub-region 81A, administration start and end dates of therapeutic drugs A and B in the second period and a bar 83 indicating the dose are displayed. In the sub-regions 81B and 81C, a line graph 84 obtained by plotting the examination values of vital signs and subject examinations in the second period for each acquisition date and connecting the examination values with a line is displayed. In the display field 77 of vital signs and subject examinations, the legend of the line graph 84 is displayed.

The bar 83 displayed in each of the sub-regions 81A to 81C and the points foil ling the line graph 84 are disposed at the positions of the medical examination data display region 76 corresponding to the administration date, the measurement date, and the examination date.

In addition to the medical examination data display region 76, a patient information display region 85 or a disease name display region 86 is provided on the medical examination data display screen 20. Character information indicating patient ID and name, date of birth, and age of a medical examination target patient is displayed on the patient information display region 85. Character information indicating a diagnostic disease name, such as "lung cirrhosis", is displayed in the disease name display region 86.

A check box 87 is provided next to the item of each examination value in the display field 77. A case search button 88 is provided below the medical examination data display region 76. The check box 87 and the case search button 88 are for inputting an instruction to distribute the graph comparison display screen 21. In a case where the check box 87 of the item of a desired examination value is selected by the cursor 80 and the case search button 88 is selected by the cursor 80, the browser control unit 36 issues a second distribution request, which includes the item of the examination value, for which the check box 87 has been selected, to the medical examination assistance server 11. FIG. 14 shows how the check box 87 of the AST item is selected.

Figure 15:
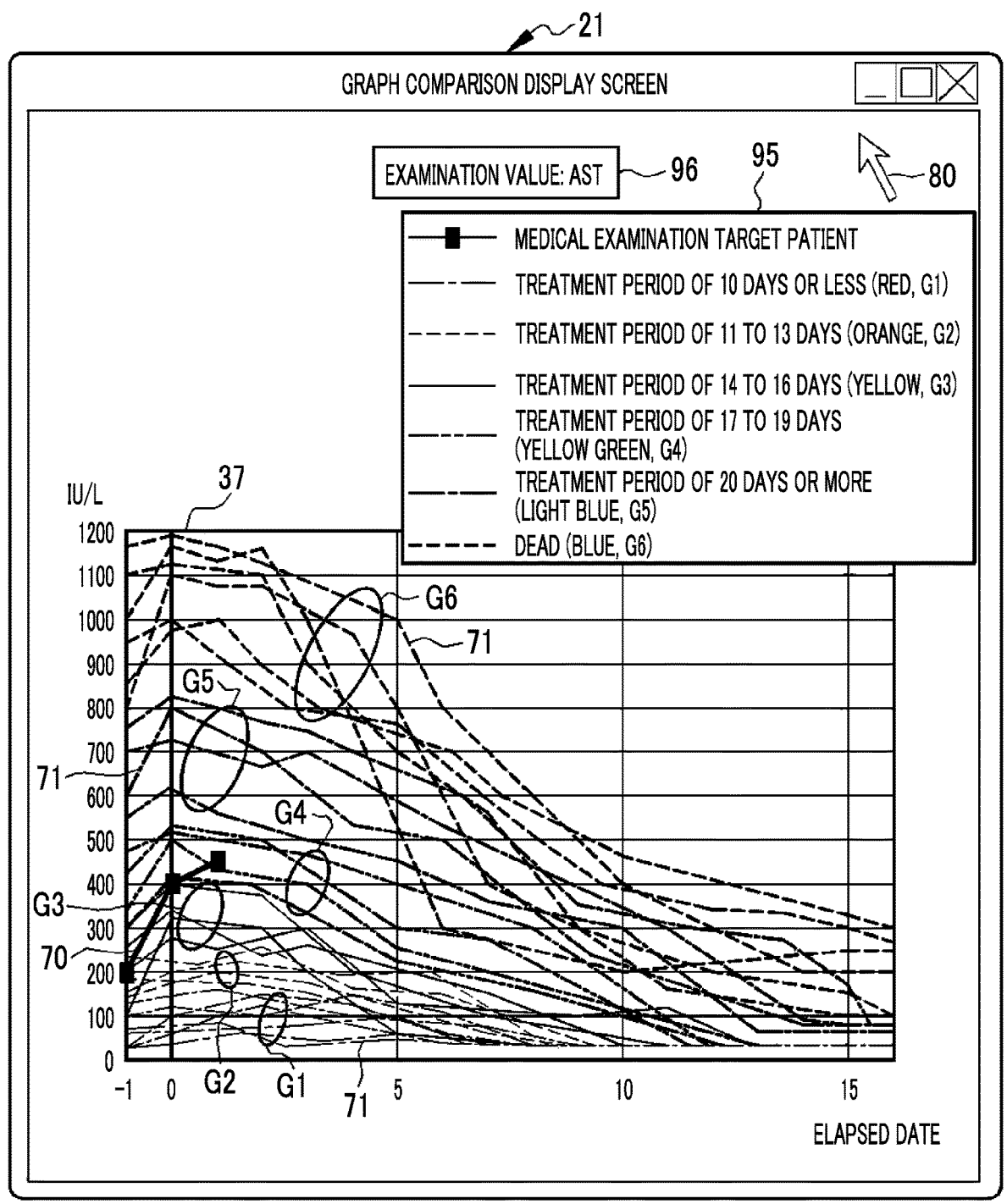
FIG. 15 is a diagram showing a graph comparison display screen.

The graph comparison display screen 21 is pop-up displayed, for example, on the medical examination data display screen 20. In FIG. 15, in the graph display region 37, the line graphs 70 and 71 are displayed so as to overlap each other as described above. These graphs 70 and 71 are displayed along the time axis with the elapsed date "0" as the reference date.

The line graph 71, which is indicated by a thin one-dot chain line and a part of which is displayed in the area indicated by the ellipse of G1, shows a time-series change in the AST examination value of the comparative case of group ID "G1-P050" whose conditions are "treatment period of 10 days or less", and is displayed in red. The line graph 71, which is indicated by a thin broken line and a part of which is displayed in the area indicated by the ellipse of G2, shows a time-series change in the AST examination value of the comparative case of group ID "G2-P050" whose conditions are "treatment period of 11 to 13 days", and is displayed in orange. The line graph 71, which is indicated by a thin solid line and a part of which is displayed in the area indicated by the ellipse of G3, shows a time-series change in the AST examination value of the comparative case of group ID "G3-P050" whose conditions are "treatment period of 14 to 16 days", and is displayed in yellow.

The line graph 71, which is indicated by a thick two-dot chain line and a part of which is displayed in the area indicated by the ellipse of G4, shows a time-series change in the AST examination value of the comparative case of group ID "G4-P050" whose conditions are "treatment period of 17 to 19 days", and is displayed in yellow green. The line graph 71, which is indicated by a thick one-dot chain line and a part of which is displayed in the area indicated by the ellipse of G5, shows a time-series change in the AST examination value of the comparative case of group ID "G5-P050" whose conditions are "treatment period of 20 days or more", and is displayed in light blue. The line graph 71, which is indicated by a thick broken line and a part of which is displayed in the area indicated by the ellipse of G6, shows a time-series change in the AST examination value of the comparative case of group ID "G6-P050" whose conditions are "dead", and is displayed in blue.

The line graph 70 of the medical examination target patient is displayed by, for example, a thick black solid line in order to avoid being embedded in the plurality of line graphs 71 of comparative cases. Here, for convenience of explanation, the line type of the line graph 71 of each group is changed. In practice, however, all of the line graphs 71 are drawn by solid lines, and only the display colors are different depending on the group. The ellipses of G1 to G6 are also attached for convenience of explanation, and the ellipses of G1 to G6 are not actually displayed.

In addition to the graph display region 37, a legend 95 and an item display region 96 is provided on the graph comparison display screen 21. Character information indicating the item of the examination value is displayed in the item display region 96. Parentheses indicating the display color and the group of the legend 95 are not actually displayed as in the ellipses of G1 to G6. The normal range of the examination value may be displayed in the graph display region 37.

FIG. 15 shows an example in which the graphs 70 and 71 are displayed for the AST examination value. In this case, the unit on the vertical axis is "international unit (IU)/L". As the elapsed date on the horizontal axis, for example, the elapsed date "−1" before the elapsed date "0", which is the reference date, to the elapsed date "16" are displayed. In addition, FIG. 15 exemplifies a case in which the graph comparison display screen 21 is displayed by outputting the second distribution request in a case where one day passes from the reference date. Therefore, the line graph 70 is discontinued since there is no examination value after the elapsed date "1".

In a case where a plurality of check boxes 87 are selected and a case search button 88 is selected and a plurality of items are included in the second distribution request, the screen display control unit 49 generates the graph comparison display screen 21 for each of the plurality of items, and the graph comparison display screen 21 of each item is displayed on the display 29A. Alternatively, the graph display region 37 may be assigned to each of the plurality of items on one graph comparison display screen 21 so that the graphs 70 and 71 of each item can be viewed on the one graph comparison display screen 21.

Figure 16:
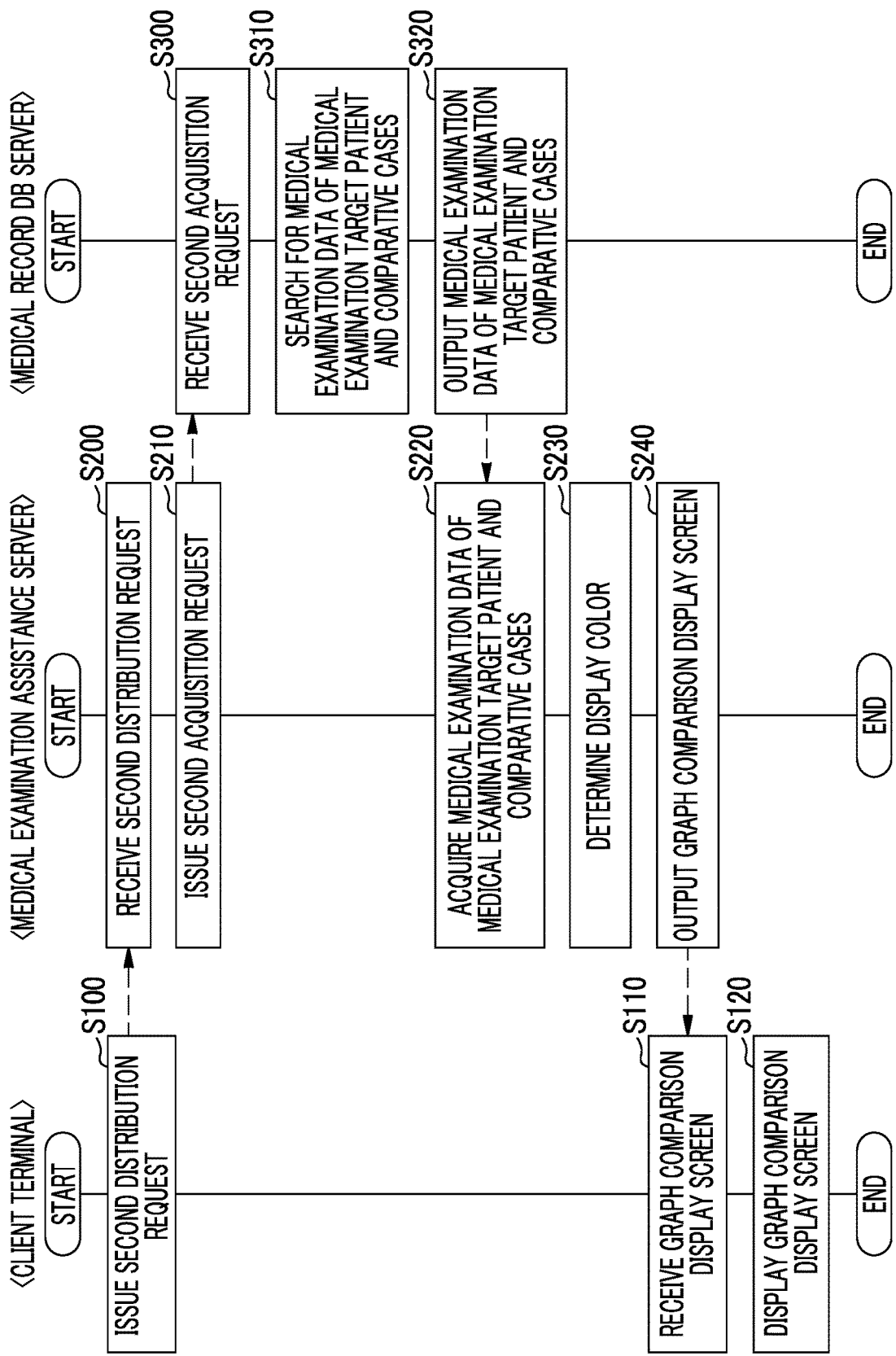
FIG. 16 is a flowchart showing the processing procedures of the CPU of the client terminal, the CPU of the medical examination assistance server, and the CPU of the medical record DB server.

Hereinafter, the operation of the above configuration will be described with reference to the flowchart shown in FIG. 16. First, a medical staff operates the client terminal 10 to input an instruction to distribute the medical examination data display screen 20 on the initial screen on the web browser. In response to the distribution instruction, a first distribution request is issued from the browser control unit 36 to the medical examination assistance server 11.

In the medical examination assistance server 11, the first distribution request is received by the reception unit 46. The patient ID of the medical examination target patient received by the first distribution request is output to the acquisition unit 47, and the first acquisition request is issued from the acquisition unit 47 to the medical record DB server 12.

In the medical record DB server 12, the first acquisition request is received by the reception unit 56. The patient ID of the medical examination target patient received by the first acquisition request is output to the search unit 57. Then, the search unit 57 searches for the medical examination data of the medical examination target patient from the electronic medical record DB 14. The searched medical examination data of the medical examination target patient is output to the medical examination assistance server 11 by the output control unit 58.

In the medical examination assistance server 11, the medical examination data of the medical examination target patient is acquired by the acquisition unit 47. The medical examination data of the medical examination target patient is output to the screen display control unit 49. In the screen display control unit 49, the medical examination data display screen 20 is generated based on the medical examination data of the medical examination target patient. The XML data of the medical examination data display screen 20 is output to the client terminal 10 that is the output source of the first distribution request.

In the client terminal 10, the XML data of the medical examination data display screen 20 is received by the browser control unit 36. The medical examination data display screen 20 to be displayed on the web browser is reproduced by the browser control unit 36 based on the XML data, and the medical examination data display screen 20 is displayed on the display 29A by the GUI control unit 35.

Various kinds of medical examination data of the medical examination target patient are displayed in time series on the medical examination data display screen 20. The medical staff browses the medical examination data display screen 20 to check the medical condition of the medical examination target patient.

On the medical examination data display screen 20, in order to check the medical condition of the medical examination target patient in more detail, the medical staff selects the check box 87 of the item of the desired examination value with the cursor 80 and selects the case search button 88 with the cursor 80. In response to the instruction to distribute the graph comparison display screen 21, as shown in step S100 of FIG. 16, the second distribution request including the item of the examination value for which the check box 87 has been selected is issued from the browser control unit 36 to the medical examination assistance server 11.

In the medical examination assistance server 11, the second distribution request is received by the reception unit 46 (step S200). The patient ID of the medical examination target patient received by the second distribution request is output to the acquisition unit 47, and the item of the examination value is output to the screen display control unit 49. The second acquisition request is issued from the acquisition unit 47 to the medical record DB server 12 (step S210).

In the medical record DB server 12, the second acquisition request is received by the reception unit 56 (step S300). The patient ID of the medical examination target patient received by the first-time second acquisition request and the CPID of the medical examination target patient received by the second-time second acquisition request are output to the search unit 57. Then, the search unit 57 searches for the medical examination data of the medical examination target patient from the electronic medical record DB 14 in response to the first-time second acquisition request, and searches for comparative cases in response to the second-time second acquisition request (step S310). These are output to the medical examination assistance server 11 by the output control unit 58 (step S320).

In the medical examination assistance server 11, the acquisition unit 47 acquires the medical examination data of the medical examination target patient and the comparative cases (step S220). The comparative cases acquired at this time are medical examination data having the same CP as the medical examination target patient. Since the CP is generated for each disease type or disease name, the comparative cases are medical examination data of patients having at least the same disease type or disease name as the medical examination target patient. In addition, since the CP is a summary of treatment plan of each day, the comparative cases have the same item of examination values as the medical examination data of the medical examination target patient as long as at least a variance does not occur. Therefore, it is possible to acquire comparative cases that are easy to be compared with the medical examination data of the medical examination target patient.

The medical examination data of the medical examination target patient and the comparative case that have been acquired by the acquisition unit 47 are output to the screen display control unit 49, and the comparative case is output to the display form determination unit 48.

Then, the display form determination unit 48 determines display colors, which are for displaying time-series changes in the examination values of a plurality of comparative cases from the acquisition unit 47 by color coding, according to the length of the treatment period and whether the patient is alive or dead (step S230). Specifically, first, for each of the comparative cases, the treatment period is calculated based on the CP application start date and the discharge date recorded in the medical examination and/or treatment records. Then, the comparative cases are assigned to groups for each condition based on the conditions and display color table 50 in which the conditions relevant to the treatment period or the like and the display color are set, and the display color designation information 66 showing the result is output to the screen display control unit 49.

The screen display control unit 49 generates the line graph 70 based on the medical examination data of the medical examination target patient from the acquisition unit 47. In addition, based on a plurality of comparative cases from the acquisition unit 47, a plurality of line graphs 71 color-coded with the respective display colors are generated while referring to the display color designation information 66 from the display form determination unit 48. The XML data of the graph comparison display screen 21 generated as described above is output to the client terminal 10 that is the output source of the second distribution request (step S240).

In the client terminal 10, the XML data of the graph comparison display screen 21 is received by the browser control unit 36 (step S110). The graph comparison display screen 21 to be displayed on the web browser is reproduced by the browser control unit 36 based on the XML data, and the graph comparison display screen 21 is displayed on the display 29A by the GUI control unit 35 (step S120).

The line graph 70 showing a time-series change in the examination value of the medical examination target patient and a plurality of line graphs 71 showing time-series changes in the examination values of a plurality of comparative cases are displayed on the graph comparison display screen 21 so as to overlap each other along the time axis with the elapsed date "0" as a reference. The plurality of line graphs 71 are color-coded and displayed with display colors designated by the display color designation information 66.

According to the graph comparison display screen 21, time-series changes in the examination values of the medical examination target patient and time-series changes in the examination values of a plurality of comparative cases can be known at a glance. Since the line graph 71 is color-coded with a display color for each group according to the length of the treatment period and whether the patient is alive or dead, it is possible to immediately determine whether or not the time-series changes in the examination values of the medical examination target patient are similar to time-series changes in the examination values of comparative cases of which group. Therefore, even an inexperienced doctor can easily and reliably ascertain the sign of deterioration of the medical condition of the medical examination target patient. Also for an experienced doctor, the display of the graph comparison display screen 21 serves as a support for predicting the future medical condition of the medical examination target patient. Therefore, this can contribute to prompt decision making.

Since the CP application start date is set as the reference date by the screen display control unit 49, the graphs 70 and 71 on the graph comparison display screen 21 can be displayed so as to overlap each other along the time axis. As a result, since it becomes easy to compare the graphs 70 and 71, it also becomes easy to determine the future medical condition of the medical examination target patient.

On the graph comparison display screen 21 shown in FIG. 15, the line graph 70 is located approximately in the middle of the line graph 71 indicated by the thin solid line of the area indicated by the ellipse of G3 and the line graph 71 indicated by the thick two-dot chain line of the area indicated by the ellipse of G4, and tends to follow the line graph 71 indicated by the thick two-dot chain line of the area indicated by the ellipse of G4. The line graph 71 indicated by the thin solid line of the area indicated by the ellipse of G3 corresponds to a case where the conditions are "treatment period of 14 to 16 days", and the line graph 71 indicated by the thick two-dot chain line of the area indicated by the ellipse of G4 corresponds to a case where the conditions are "treatment period of 17 to 19 days". Therefore, it can be seen that there is a possibility that the treatment period can be shortened from "17 to 19 days" to "14 to 16 days" by taking appropriate measures at this point in time. In this manner, since it is possible to predict the future medical condition of the medical examination target patient, it is possible to apply appropriate treatment to the medical examination target patient in advance. Since this can contribute to improving the treatment outcome, a very good result can also be obtained for the medical examination target patient. In addition, by comparison with a time-series change in the examination value of the comparative case, it is possible to predict the transition of the examination value of the medical examination target patient and the treatment period. Being able to predict the transition of the examination value of the medical examination target patient and the treatment period helps to determine the next visit date to ascertain the prediction results of the transition of the examination value and the treatment period in the case of an outpatient, and helps to determine the next examination date in the case of an inpatient.

In a case where the line graph 70 follows the line graph 71 in a case where the treatment outcome is relatively bad, such as the line graph 71 indicated by the thick one-dot chain line of the area indicated by the ellipse of G5 whose conditions are "treatment period of 20 days or more" or the line graph 71 indicated by the thick broken line of the area indicated by the ellipse of G6 whose conditions are "dead", it can be seen that it is necessary to perform treatment as soon as possible. In a case where the line graph 70 follows the line graph 71 in a case where the treatment outcome is relatively good, such as the line graph 71 indicated by the thin one-dot chain line of the area indicated by the ellipse of G1 whose conditions are "treatment period of 10 days or less", it can be seen that the current treatment policy may be continued.

In the first embodiment described above, the graphs 70 and 71 are generated only for the items of examination values included in the second distribution request. However, the graphs 70 and 71 may be generated for all items of examination values in the case of generating the medical examination data display screen 20 in response to the first distribution request. In this case, there is no need to transmit and receive the second distribution request between the client terminal 10 and the medical examination assistance server 11. In addition, in this case, each item of the examination value can be selected by the cursor 80 in the display field 77 of the medical examination data display screen 20, and the graph comparison display screen 21 of the item selected by the cursor 80 is selectively displayed.

In the first embodiment described above, the medical examination data display screen 20 and the graph comparison display screen 21 are separate display screens. However, the graph display region 37 may be provided on the medical examination data display screen 20, and the medical examination data display screen 20 and the graph comparison display screen 21 may be integrated into one display screen. For example, instead of displaying the line graphs 84 of a plurality of items collectively, such as in the sub-region 81B where the line graphs 84 of a plurality of items of vital signs are collectively displayed or the sub-region 81C where the line graphs 84 of a plurality of items of the subject examination are collectively displayed in the medical examination data display screen 20 shown in FIG. 14, the display regions of the line graphs 84 are clearly divided for each item, the line graphs 84 are displayed in separate display regions, and the graph display regions 37 are displayed side by side in the display region of each item. In this manner, since time-series changes in other items not selected by the check box 87 can also be viewed on the same display screen, comparison with the other items becomes easy.

On the other hand, in a case where the number of items selected by the check box 87 is relatively large, in a case where the medical examination data display screen 20 and the graph comparison display screen 21 are integrated into one display screen, the graph display region 37 is reduced so that a plurality of graph display regions 37 are included in a limited screen region, or the number of non-display portions is increased since the plurality of graph display regions 37 cannot be included at once. Since this makes it difficult to see the display screen, it is preferable to display the medical examination data display screen 20 and the graph comparison display screen 21 separately as in the first embodiment described above. A display mode in which the medical examination data display screen 20 and the graph comparison display screen 21 are separate display screens and a display mode in which the medical examination data display screen 20 and the graph comparison display screen 21 are integrated into one display screen may be switchable.

Alternatively, in the case of integrating the medical examination data display screen 20 and the graph comparison display screen 21, a display switching button for switching display and non-display of the graph display region 37 may be provided on the medical examination data display screen 20, so that switching between the display and non-display of the graph display region 37 is performed according to the operation of the display switching button. In a case where there are a plurality of items selected by the check box 87, display and non-display of the graph display region 37 may be switchable for each item.

Figure 17:
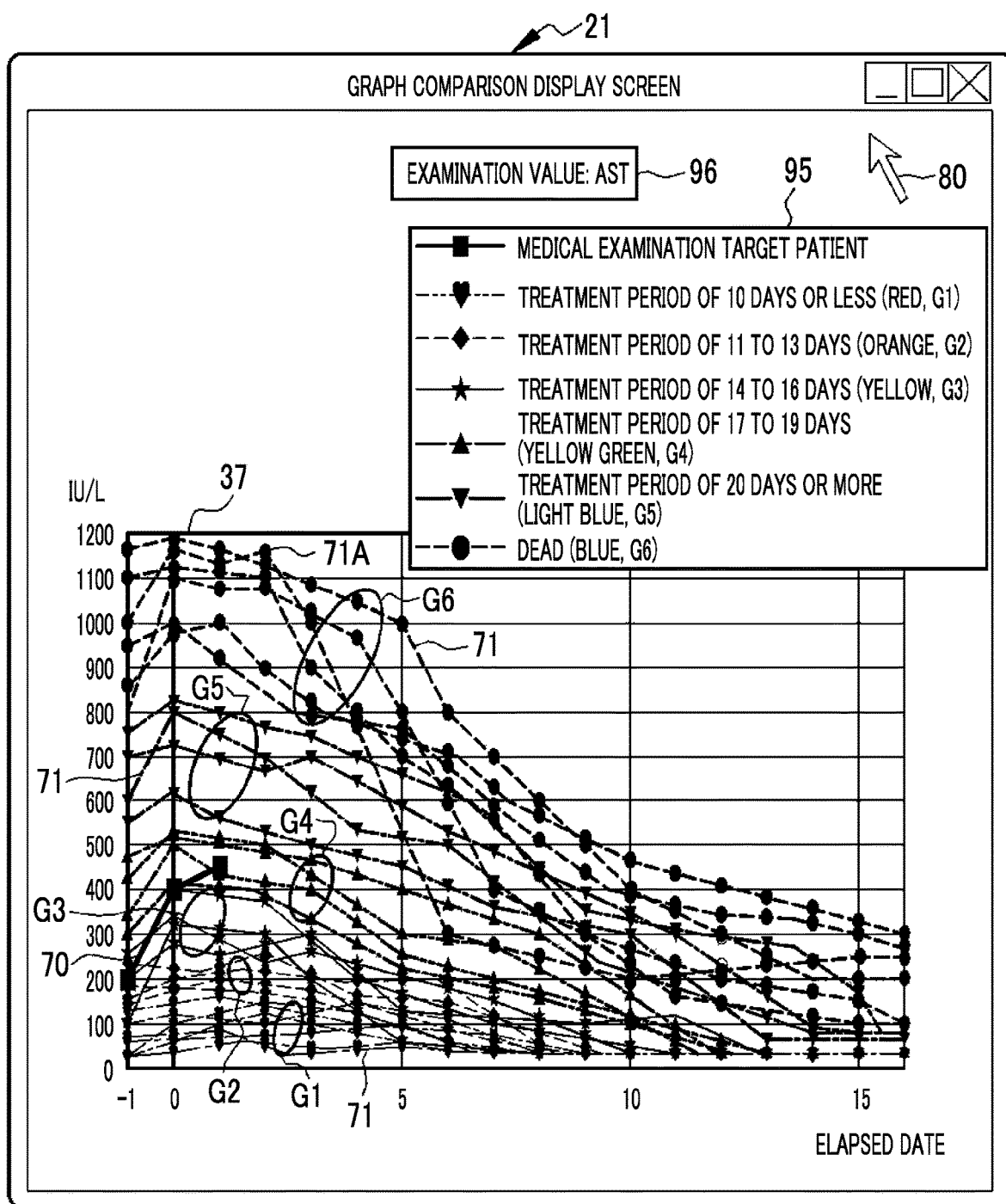
FIG. 17 is a diagram showing a graph comparison display screen obtained by adding points to line graphs showing time-series changes in the examination values of comparative cases.
Figure 18:
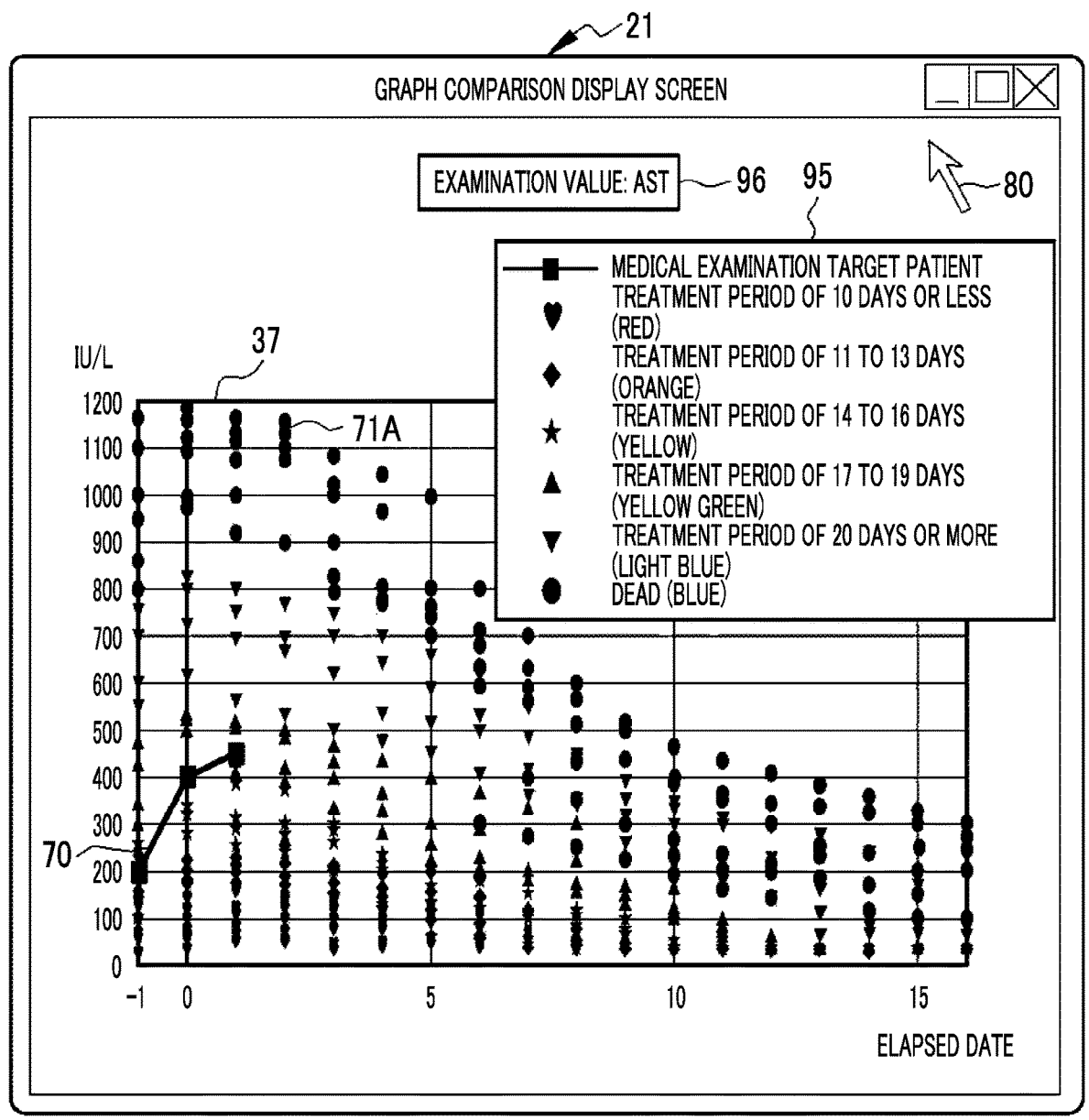
FIG. 18 is a diagram showing a graph comparison display screen in which time-series changes in the examination values of comparative cases are shown only by points.

In the first embodiment described above, the point 70A is plotted only on the line graph 70. However, as shown in FIG. 17, a point 71A may be plotted on the line graph 71. Alternatively, as shown in FIG. 18, only the point 71A may be displayed without displaying the line graph 71. In these cases, the point 71A may be color-coded and displayed with the same display color as the line of the line graph 71. By plotting a plurality of points 71A indicating the examination values of comparative cases for each acquisition date in this manner, the distribution of examination values of each group can be seen at a glance.

In FIGS. 17 and 18, for convenience of explanation, the type of the point 71A is changed for each group, such as the heart mark point 71A for a group whose conditions are "treatment period of 10 days or less" or the rhombic point 71A for a group whose conditions are "treatment period of 11 to 13 days". In practice, however, the points 71A of the same type (for example, round points) are color-coded and displayed according to the display color.

Second Embodiment

In the first embodiment described above, the display color is determined according to the length of the treatment period. However, the present invention is not limited thereto. In the case of a patient adopting the CP, it is possible to determine whether the treatment outcome is good or bad according to the variance. Therefore, in the present embodiment, the display color is determined according to the variance.

More specifically, the display form determination unit 48 of the present embodiment determines the display color according to the number of positive variance occurrences, the number of negative variance occurrences, and the life and death of a patient. Here, the positive variance is a variance occurring in a case where the recovery of a patient is better than that assumed in the treatment plan. The negative variance is a variance occurring in a case where the recovery of a patient is not better than that assumed in the treatment plan. Examples of the positive variance include a case where the treatment plan is made earlier than planned and a case where a part of the treatment plan is determined to be unnecessary and omitted. Examples of the negative variance include a case where the treatment plan is delayed than planned and a case where complications develop and a treatment plan, which is not included in the original treatment plan, is added.

Figure 19:
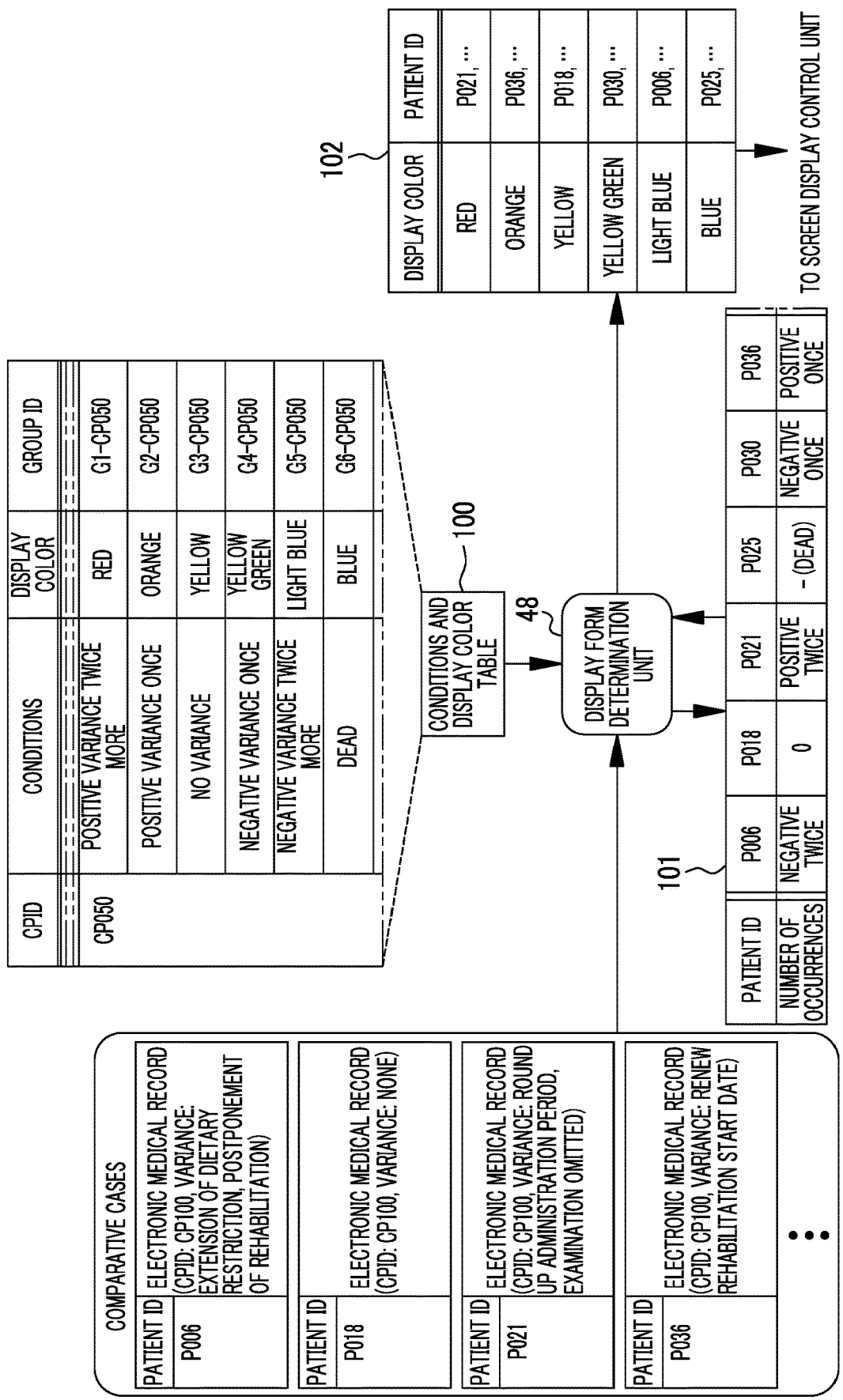
FIG. 19 is a diagram illustrating the display form determination function of a display form determination unit in a second embodiment.

FIG. 19 shows how to determine the display colors of comparative cases, such as patient IDs "P006", "P018", "P021", and "P036". In a conditions and display color table 100 in this case, the number of variance occurrences and conditions corresponding to the life and death of the patient, such as "positive variance twice or more", "no variance", and "dead", are registered.

The display form determination unit 48 generates intermediate processing data 101 instead of the intermediate processing data 65. The intermediate processing data 101 is obtained by counting the number of positive variance occurrences and the number of negative variance occurrences recorded in the medical examination and/or treatment records and associating the counted number of occurrences with the patient ID of the comparative case for each of the comparative cases from the acquisition unit 47.

For example, in the case of a comparative case of patient ID "P006", since two negative variances of "extension of dietary restriction and postponement of rehabilitation" are recorded in the medical examination and/or treatment records, the number of negative variance occurrences "twice" is counted. In the case of a comparative case of patient ID "P021", since two positive variances of "administration period rounded up, examination omitted" are recorded in the medical examination and/or treatment records, the number of positive variance occurrences "twice" is counted. Similarly to the case of the intermediate processing data 65, in a case where the patient dies as in the comparative case of patient ID "P025", the display form determination unit 48 does not count the number of variance occurrences.

The display form determination unit 48 compares the number of variance occurrences of the intermediate processing data 101 with the conditions in the conditions and display color table 100, and assigns each comparative case to a group corresponding to the conditions. The display form determination unit 48 generates display color designation information 102 that summarizes the allocation result of comparative cases. Similarly to the display color designation information 66, in the display color designation information 102, the patient ID of the comparative case assigned to each group is written so as to correspond to the display color. For example, since the number of variance occurrences of the comparative case of the patient ID "P006" is "negative twice (the number of negative variance occurrences is twice)", the patient ID "P006" is written in the display color "light blue" in a case where the conditions are "negative variance twice or more". In addition, since the number of variance occurrences of the comparative case of the patient ID "P021" is "positive twice (the number of positive variance occurrences is twice)", the patient ID "P021" is written in the display color "red" in a case where the conditions are "positive variance twice or more". The display color may also be determined, for example, according to the difference between the number of positive variance occurrences and the number of negative variance occurrences, which is obtained by subtracting the number of negative variance occurrences from the number of positive variance occurrences.

Instead of the method of determining the display color according to the length of the treatment period in the first embodiment or the variance in the second embodiment, the display color may be determined according to the level of the examination value on the elapsed date after the reference date. For example, on the elapsed date "10", blue is determined in a case where the AST examination value is "401 to 500" and orange is determined in a case where the AST examination value is "301 to 400". That is, the display color may be determined based on some criteria for determining whether or not the treatment outcome is good or bad. There is no particular limitation on what to use for criteria, and any criteria may be used.

Third Embodiment

The display form of the comparative case result information is not limited to the line graph 71 or the point 71A in the first embodiment described above. In the present embodiment, a heat map is generated as comparative case result information.

Figure 20:
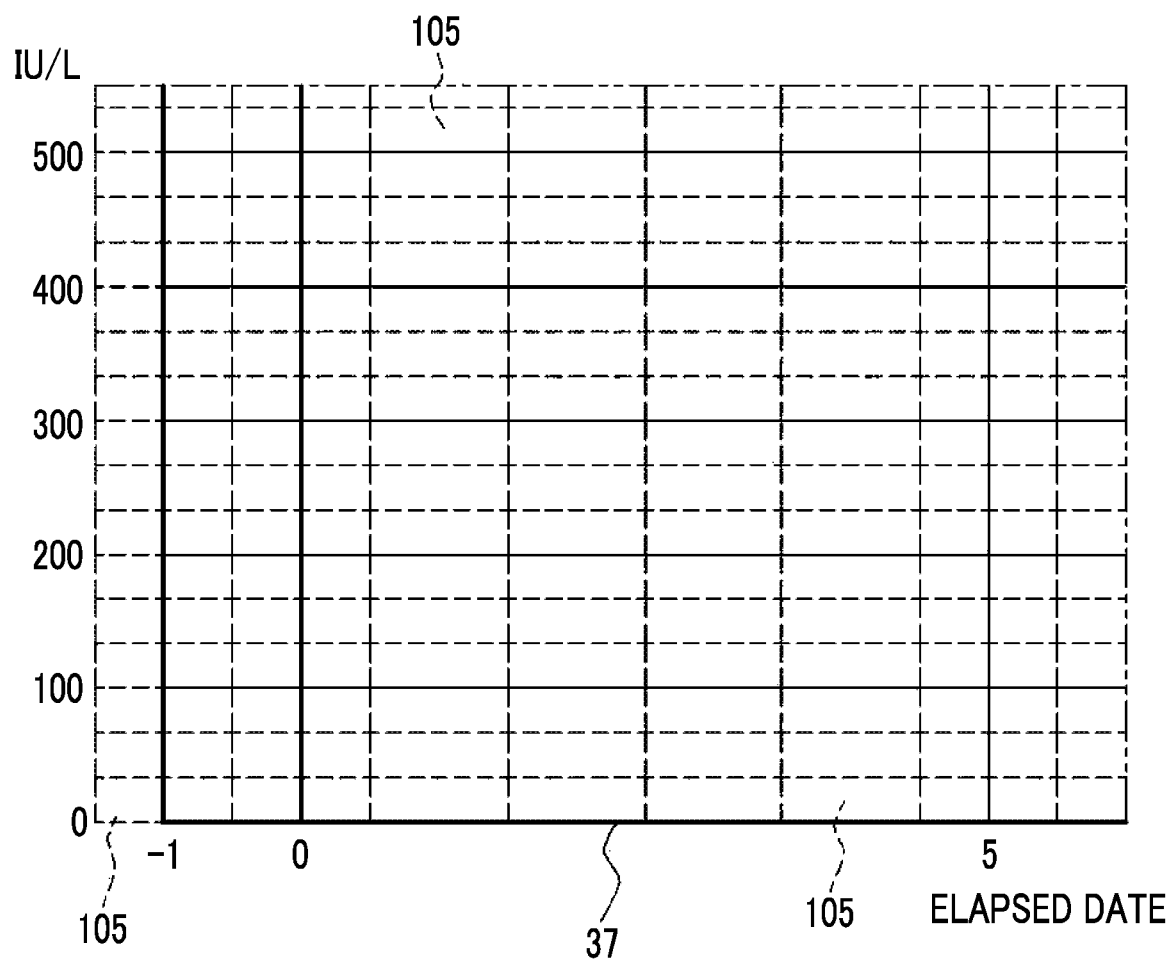
FIG. 20 is a diagram showing a rectangular region set in a graph display region.

As shown in FIG. 20, the display form determination unit 48 sets a plurality of rectangular regions 105 by dividing the graph display region 37 by the examination value unit on the vertical axis and the elapsed date (acquisition date) unit on the horizontal axis. Here, as in FIG. 15 or the like, the graph display region 37 of the AST examination value is exemplified.

Then, the display form determination unit 48 determines the display color of each comparative case as in the first embodiment described above. Thereafter, for each of the rectangular regions 105, the display form determination unit 48 determines which line graph 71 (examination value) of which comparative case, among the line graphs 71 (examination values) of respective comparative cases, is present.

After the end of the determination of all of the rectangular regions 105, the display form determination unit 48 calculates an average color (average value of treatment outcomes), which is an average of display colors of the line graphs 71 present in the respective rectangular regions 105, as an index value, and determines the calculated average color as a display color of each rectangular region 105. For example, in a case where the red line graph 71 and the blue line graph 71 are present in a certain rectangular region 105, the display color of the rectangular region 105 is purple that is an average color of red and blue.

For the rectangular region 105 where the line graph 71 is not present, the display color may be determined based on the rectangular region 105 around the rectangular region 105. In the determination of the display color of the rectangular region 105 where such a line graph 71 is not present, it is possible to apply a general pixel complement technique for complementing the pixel value of a defective pixel with the pixel values of surrounding pixels in the case of generating an image. Specifically, any method may be used. Alternatively, the display color of the rectangular region 105 where the line graph 71 is not present may be the same color (for example, an achromatic color such as white or gray) as the background of the graph display region 37.

Figure 21:
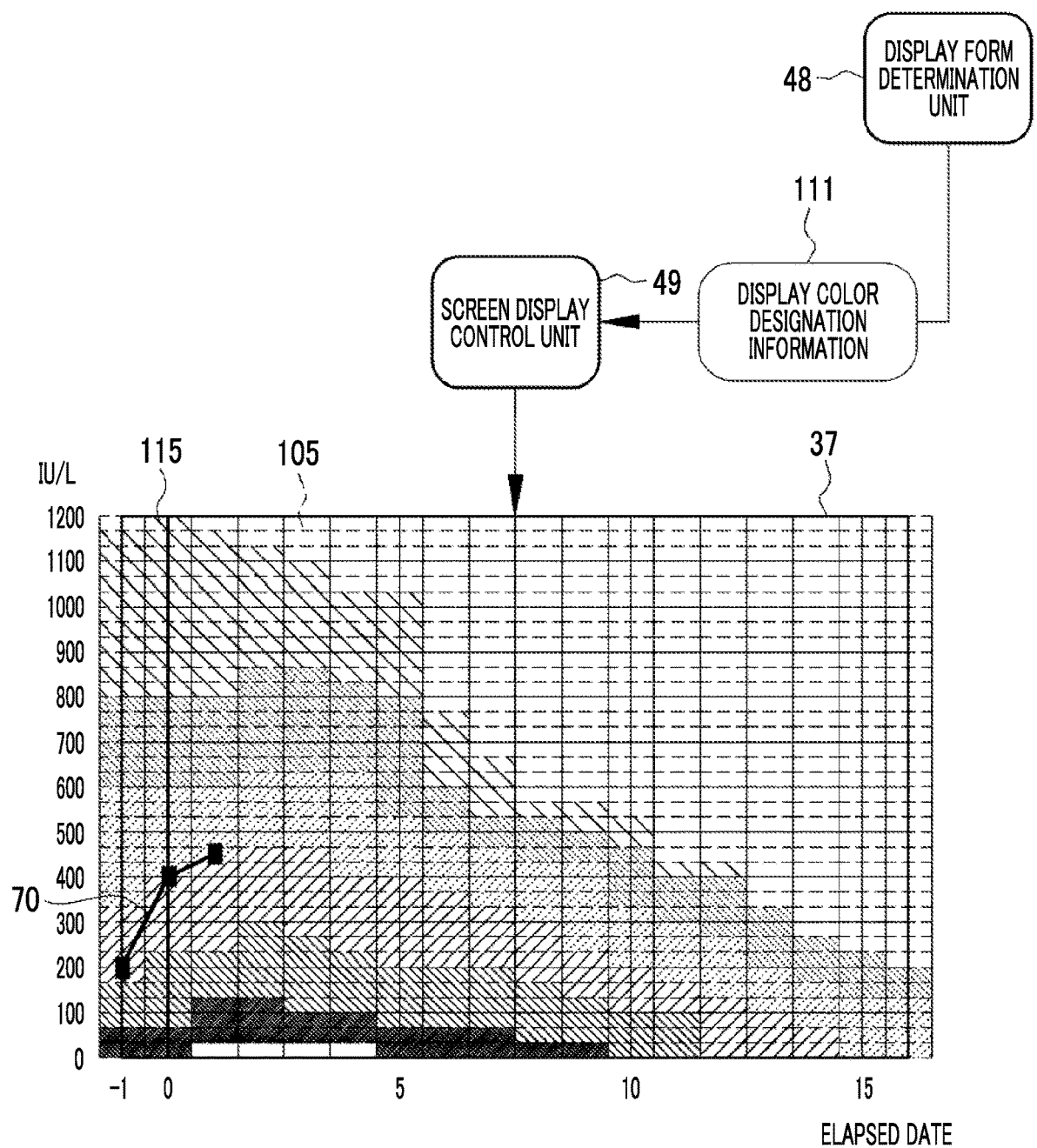
FIG. 21 is an explanatory diagram conceptually showing the heat map generation processing of a screen display control unit.

In FIG. 21, the display form determination unit 48 generates display color designation information 111 that summarizes the determination result of the display color of each rectangular region 105. As described with reference to FIG. 12, the screen display control unit 49 generates the line graph 70 in the graph display region 37 based on the medical examination data of the medical examination target patient from the acquisition unit 47. Based on the display color designation information 111 from the display form determination unit 48, the screen display control unit 49 generates a heat map 115 as comparative case result information by color-coding the rectangular region 105 with the display color designated by the display color designation information 111.

By generating the line graph 70 and the heat map 115 in the graph display region 37 as described above by the screen display control unit 49, the line graph 70 and the heat map 115 are eventually displayed so as to overlap each other in the graph display region 37. In the first embodiment described above, the comparative case is output from the acquisition unit 47 to the screen display control unit 49. In the present embodiment, however, since the heat map 115 is displayed instead of the line graph 71 of the comparative case, no comparative case is output from the acquisition unit 47 to the screen display control unit 49.

Figure 22:
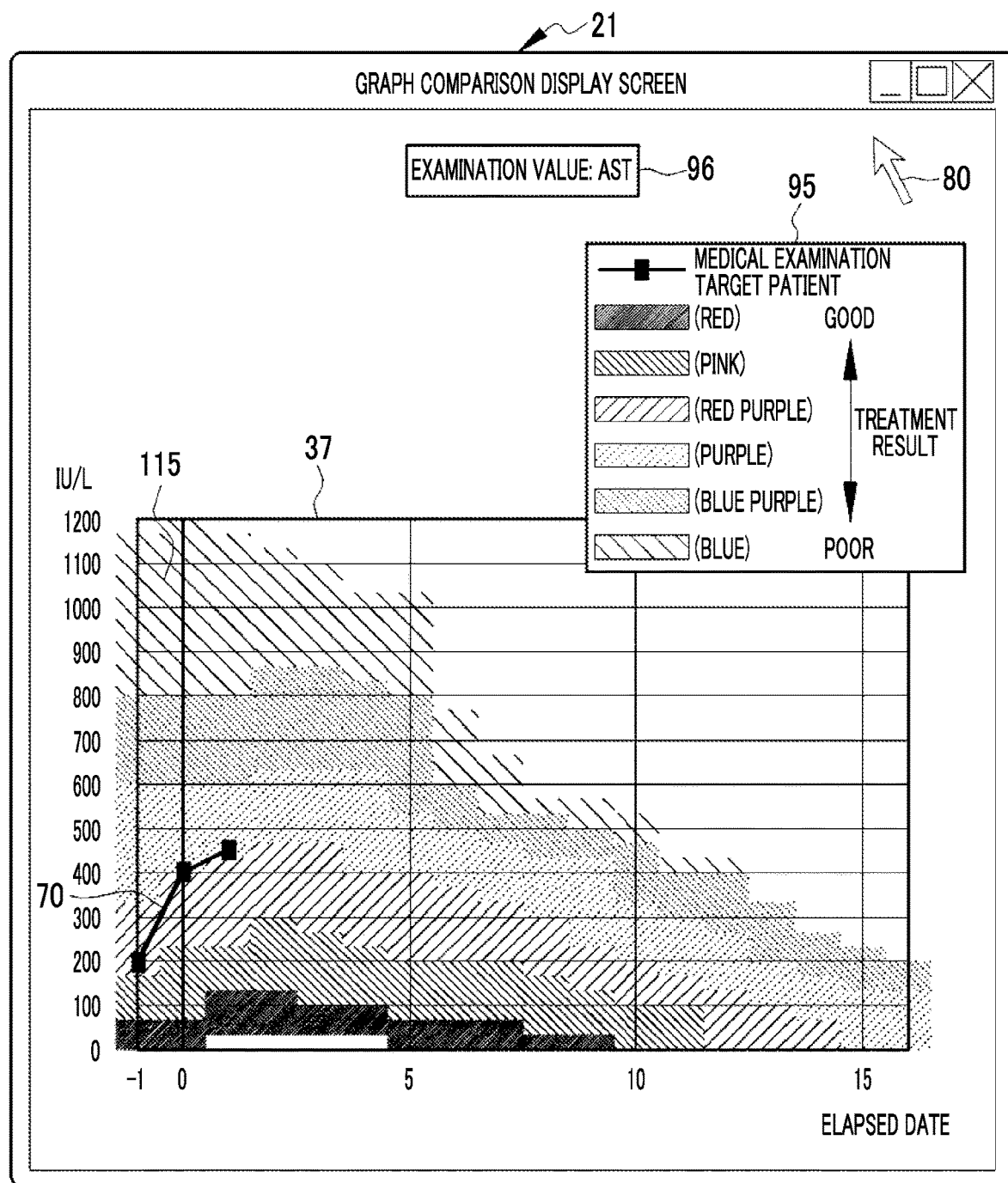
FIG. 22 is a diagram showing a graph comparison display screen in a third embodiment.

In FIG. 22, in the graph display region 37 of the graph comparison display screen 21 of the present embodiment, the line graph 70 and the heat map 115 are displayed so as to overlap each other as described above. According to the graph comparison display screen 21, as in the first embodiment described above, it is possible to predict the future medical condition of the medical examination target patient. Therefore, it is possible to apply appropriate treatment to the medical examination target patient in advance.

In the case of the first embodiment described above, since a plurality of line graphs 71 or points 71A are displayed as comparative case graphs, a slightly complicated impression is given. In the present embodiment, however, since the heat map 115 is displayed as a comparative case, the display becomes clear compared with the case of the first embodiment. As a result, the medical examination becomes easier.

In addition, since the display color of each rectangular region 105 is determined based on the average color of the display color of the line graph 71, continuous gradation tends to occur. As a result, it becomes easy to predict the future medical condition of the medical examination target patient.

The average value of treatment outcomes is not limited to the average color of the display color of the line graph 71 in which each rectangular region 105 is present, and may be the average value of treatment periods. In this case, similarly to the intermediate processing data 65 of the first embodiment described above, the display form determination unit 48 calculates a treatment period for each comparative case from the acquisition unit 47, and calculates an average value of the treatment periods of the comparative cases, in which examination values are present in the rectangular region 105, for each rectangular region 105. Then, based on the conditions corresponding to the length of the average value of the treatment periods, such as "treatment period average value less than 10 days" and "treatment period average value of 10 days more and less than 12 days", and a conditions and display color table in which display colors corresponding thereto are registered, the display color of each rectangular region 105 is determined.

In FIG. 21, for convenience of explanation, the rectangular region 105 is shown. However, as shown in FIG. 22, the rectangular region 105 is not displayed on the graph comparison display screen 21, and only the line graph 70 and the heat map 115 are displayed. In addition, although the hatching form of the heat map 115 is changed according to whether the treatment outcome is good or bad, all of the rectangular regions 105 that form the heat map 115 are filled with the display color in practice. The method of setting the rectangular region 105 is not limited to the example shown in FIG. 20.

Instead of the method of calculating the average value of treatment periods exemplified above as an index value, a ratio (the number of good cases/the number of poor cases, referred to as a number-of-cases ratio) between the number of comparative cases with good treatment outcomes and the number of comparative cases with poor treatment outcomes may be calculated as an index value of the treatment outcome. In this case, the display form determination unit 48 classifies comparative cases, in which the time-series change in the examination value is indicated by the line graph 71 present in each rectangular region 105, into good and poor cases for each rectangular region 105 based on the case distribution conditions set in advance, and counts the number of good cases and the number of poor cases for each rectangular region 105. Then, the number-of-cases ratio is calculated for each rectangular region 105.

The case allocation conditions are conditions for dividing comparative cases into two groups of good cases and poor cases with a certain treatment period as a threshold value. Similarly to the conditions and display color table, the case allocation conditions are stored in the storage device 25B in a data table format in which conditions are registered for each CPID. The threshold value of the treatment period may be set based on the standard treatment period set by the CP or the average treatment period for each disease type or disease name announced by the public institution, or the same value may be set uniformly regardless of the CP, disease type, or disease name.

The number-of-cases ratio becomes larger as the number of good cases with respect to the number of poor cases becomes larger, and conversely, becomes smaller as the number of good cases with respect to the number of poor cases becomes smaller. For example, in a case where the number of good cases is "150" and the number of poor cases is "2", the number-of-cases ratio is 150/2, that is, "75". On the other hand, in a case where the number of good cases is "100" and the number of poor cases is "125", the number-of-cases ratio is 100/125, that is, "0.8". In a case where the number of poor cases is "0", the number-of-cases ratio is mathematically impossible (no solution). In this case, however, the number-of-cases ratio is converted into "100".

In the conditions and display color table in this case, conditions corresponding to the number-of-cases ratio, such as "number-of-cases ratio of 100 or more" and "number-of-cases ratio of 50 or more and less than 100", and display colors corresponding thereto are registered. The display form determination unit 48 determines the display color of each rectangular region 105 by comparing the calculated number-of-cases ratio with the conditions in the conditions and display color table. By determining the display color using the number-of-cases ratio, it is possible to generate the heat map 115 reflecting the quality of the treatment outcome more.

Figure 23:
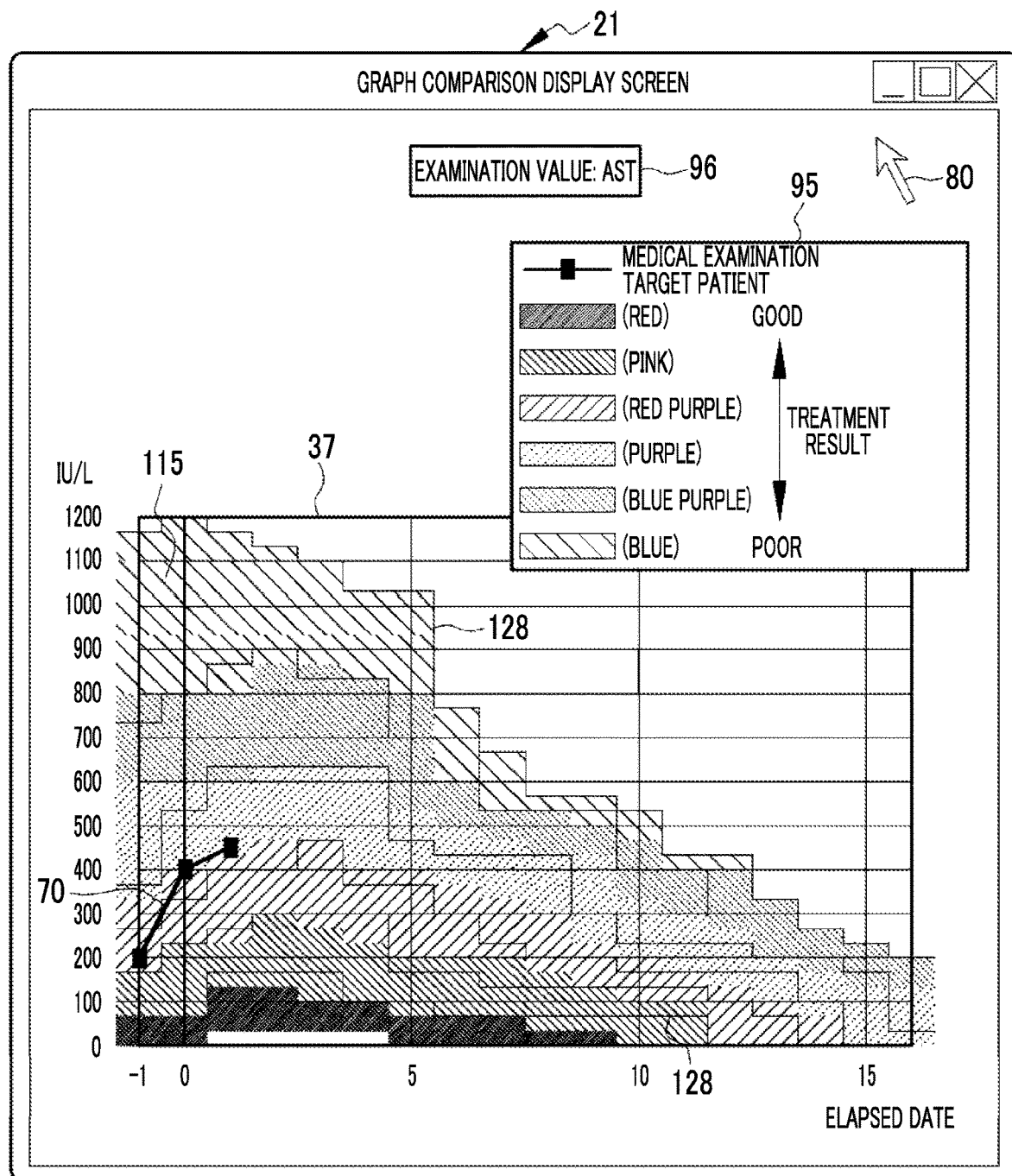
FIG. 23 is a diagram showing a graph comparison display screen where the distribution of the number of comparative cases is displayed on a heat map.

The distribution of the number of comparative cases may be displayed on the heat map 115. For example, as shown on the graph comparison display screen 21 shown in FIG. 23, an isoplethic curve 128 in which the range of the number of comparative cases indicates the boundary of the rectangular region 105 may be displayed in the heat map 115. Displaying the distribution of the number of comparative cases in this manner helps to predict the future medical condition of the medical examination target patient since it is possible to see the tendency of good or poor treatment outcome of the comparative case.

The display and non-display of the isoplethic curve 128 may be switchable, or character information indicating the range of the number of comparative cases, such as "1 to 100" and "501 to 600", may be displayed together. As a display method of the distribution of the number of comparative cases, other methods may be used, such as displaying character information indicating the number of comparative cases in each one of the rectangular regions 105, changing the number of dots of the display color according to the number of comparative cases, reducing the concentration of the display color in a case where the number of comparative cases is small, and increasing the concentration of the display color in a case where the number of comparative cases is large.

The method of determining the display color according to the variance in the second embodiment described above may be applied to the case of determining the display color of the heat map 115 in the third embodiment described above. For example, instead of the average value of the treatment periods, an average value of differences between the number of positive variance occurrences and the number of negative variance occurrences may be calculated for each rectangular region 105, and this may be used as an index value of the treatment outcome.

Alternatively, comparative cases may be divided into two groups of good cases and poor cases according to the variance, the number of good cases and the number of poor cases may be counted, and a number-of-cases ratio therebetween may be calculated as an index value of the treatment outcome. Specifically, comparative cases in which the difference between the number of positive variance occurrences and the number of negative variance occurrences is 0 or more are assigned as good cases, and comparative cases in which the difference between the number of positive variance occurrences and the number of negative variance occurrences is less than 0 are assigned as poor cases. The comparative cases in which the difference between the number of positive variance occurrences and the number of negative variance occurrences is 0 or more are comparative cases having no variance, comparative cases in which only positive variance has occurred, or comparative cases in which the number of positive variance occurrences is larger than the number of negative variance occurrences. The comparative cases in which the difference between the number of positive variance occurrences and the number of negative variance occurrences is less than 0 are comparative cases in which only negative variance has occurred, or comparative cases in which the number of negative variance occurrences is larger than the number of positive variance occurrences.

Fourth Embodiment

In the first embodiment described above, medical examination data having the same CP as a medical examination target patient is acquired as a comparative case. In the present embodiment, however, as shown in FIG. 24, medical examination data having the same surgical contents as a medical examination target patient is acquired as a comparative case.

Figure 24:
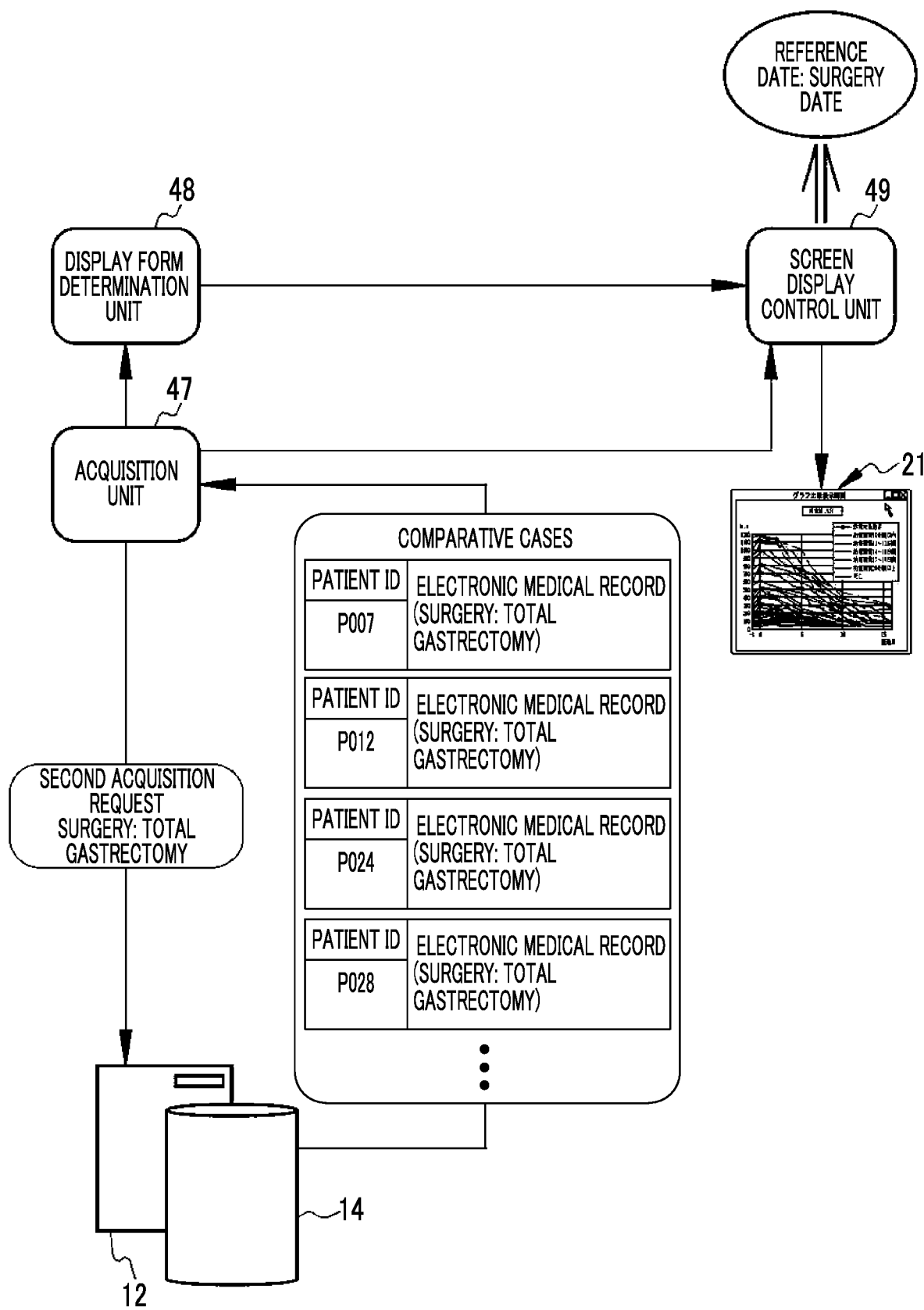
FIG. 24 is a diagram illustrating the acquisition function of an acquisition unit in a fourth embodiment.

FIG. 24 exemplifies a case in which the surgical contents "total gastrectomy" are recorded in the examination and/or treatment records of the electronic medical record of the medical examination target patient. In this case, the acquisition unit 47 outputs a second acquisition request including the surgical contents "total gastrectomy" to the medical record DB server 12. In the medical record DB server 12, the search unit 57 searches for the medical examination data of the electronic medical record of patients (patients with patient IDs "P007", "P012", and the like) in which the surgical contents "total gastrectomy" are recorded in the medical examination and/or treatment records, as a comparative case, from the electronic medical record of each patient of the electronic medical record DB 14.

Figure 25:
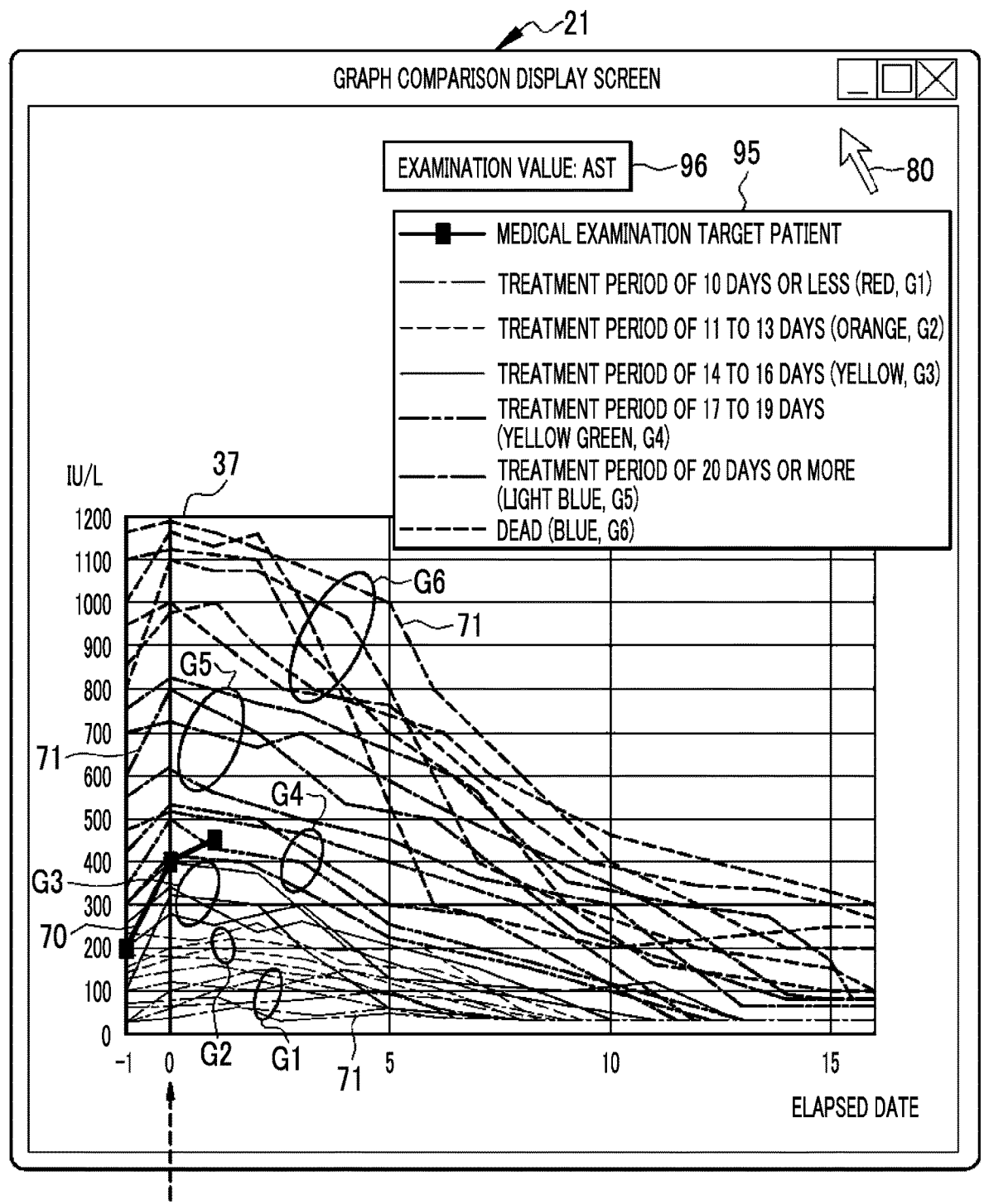
FIG. 25 is a diagram showing a graph comparison display screen in the fourth embodiment.

In this case, the surgery date is set as a reference date by the screen display control unit 49. Therefore, in the case of displaying the graphs 70 and 71 so as to overlap each other, the graphs 70 and 71 are displayed along the time axis with the surgery date as the elapsed date "0", as shown in FIG. 25. The same also applies to a case where the line graph 70 and the point 71A are displayed so as to overlap each other.

The surgical contents are information indirectly indicating the disease type or disease name. For example, in a case where the surgical contents are "total gastrectomy" in FIG. 24, it can be seen that the disease name is gastric cancer. In a case where the surgical contents are "right hepatic lobectomy", it can be seen that the disease name is liver cancer. Accordingly, as in the case of the first embodiment described above, comparative cases acquired by the acquisition unit 47 are medical examination data of patients having at least the same disease type or disease name as the medical examination target patient. If the disease type or the disease name is the same, the items of examination values are also approximately the same between comparative cases and the medical examination data of the medical examination target patient. Therefore, it is possible to acquire comparative cases that are easy to be compared with the medical examination data of the medical examination target patient.

As the surgical contents, the contents of the procedure, such as laparotomy, endoscopic mucosal resection (EMR), endoscopic submucosal dissection (ESD), and laparoscopy and endoscopy cooperatives surgery (LECS), may be included.

Fifth Embodiment

In the present embodiment, medical examination data having the same disease name and therapeutic drug as a medical examination target patient is acquired as a comparative case. In this case, a disease name and therapeutic drug table 130 shown in FIG. 26 is recorded in the storage device 25B of the medical examination assistance server 11.

In FIG. 26, in the disease name and therapeutic drug table 130, the disease name is classified for each disease type, and a collection of therapeutic drugs are shown for each disease name. FIG. 26 shows an example in which the disease type of pneumonia is classified into "standard pneumonia" and "atypical pneumonia", disease names "pneumococcal pneumonia", "Klebsiella pneumonia pneumonia", and "Staphylococcus aureus pneumonia" are classified into "standard pneumonia", and disease names "*Pseudomonas aeruginosa* pneumonia", "mycoplasma pneumonia", and "chlamydia pneumonia" are classified into "atypical pneumonia". Also for diseases other than the pneumonia shown in the diagram, disease names and their therapeutic drugs classified according to the disease type are registered in the disease name and therapeutic drug table 130. For example, in a case where the disease is hepatitis, the disease type is classified into "viral hepatitis" and "other hepatitis", "hepatitis A", "hepatitis B", and the like are classified into "viral hepatitis", and "alcoholic hepatitis", "autoimmune hepatitis", and the like are classified into "other hepatitis".

"Pneumococcal pneumonia" and "Klebsiella pneumonia pneumonia" of "standard pneumonia" have the same therapeutic drugs. In addition, "mycoplasma pneumonia" and "chlamydia pneumonia" of "atypical pneumonia" have the same therapeutic drugs. Therapeutic drugs "penicillin type A, B, C, . . . ", "macrolide type P, Q, R, . . . ", and the like have almost the same ingredients and efficacy except only that the pharmaceutical companies are different, for example. The acquisition unit 47 regards disease names having the same disease type and therapeutic drugs as the same type of disease names, and regards the therapeutic drugs as the same type of therapeutic drugs.

Figure 27:
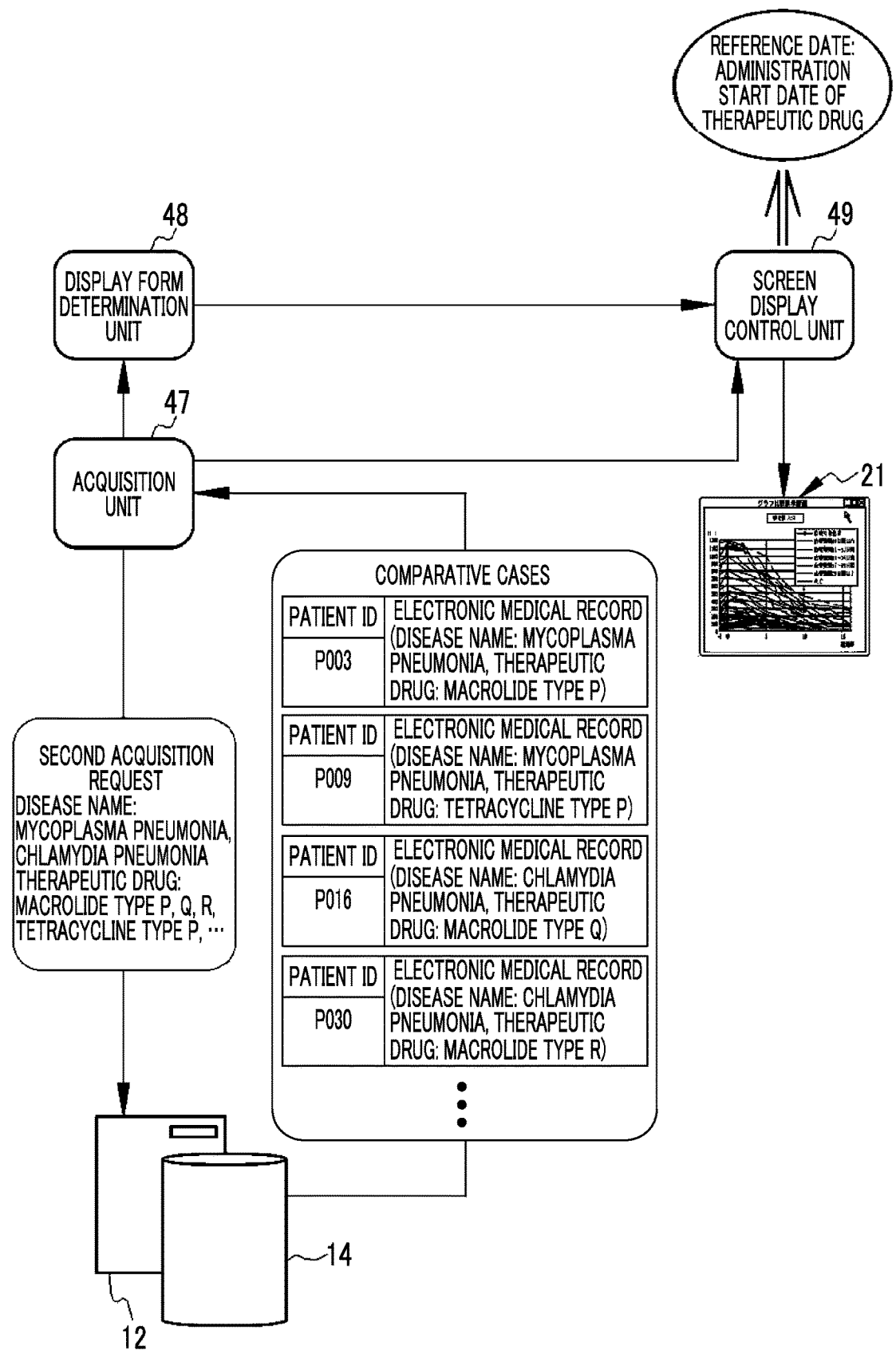
FIG. 27 is a diagram illustrating the acquisition function of an acquisition unit in a fifth embodiment.

As shown in FIG. 27, in a case where the disease name "mycoplasma pneumonia" and the therapeutic drug "macrolide type P" are recorded in the medical examination and/or treatment records of the electronic medical record of the medical examination target patient, the acquisition unit 47 outputs a second acquisition request, which includes the disease name "mycoplasma pneumonia" and the therapeutic drug "macrolide type P" and the disease name ("chlamydia pneumonia") and the therapeutic drugs ("tetracycline type P", "macrolide type Q", "macrolide type R", and the like) of the same type as the disease name "mycoplasma pneumonia" and the therapeutic drug "macrolide type P", to the medical record DB server 12 with reference to the disease name and therapeutic drug table 130.

In the medical record DB server 12, the search unit 57 searches for medical examination data of the electronic medical record of patients (patients with patient IDs "P003", "P009", and the like), in which the disease name "mycoplasma pneumonia" or the disease name "chlamydia pneumonia" of the same type as the disease name "mycoplasma pneumonia" and the therapeutic drug "macrolide type P" or the therapeutic drugs "tetracycline type P", "macrolide type Q", "macrolide type R", and the like of the same type as the therapeutic drug "macrolide type P" are recorded in the medical examination and/or treatment records, as a comparative case. That is, medical examination data having the same disease name and therapeutic drugs as the medical examination target patient includes medical examination data having completely the same disease name and therapeutic drugs as the medical examination target patient and medical examination data having the same type of disease name and therapeutic drugs as the medical examination target patient.

Figure 28:
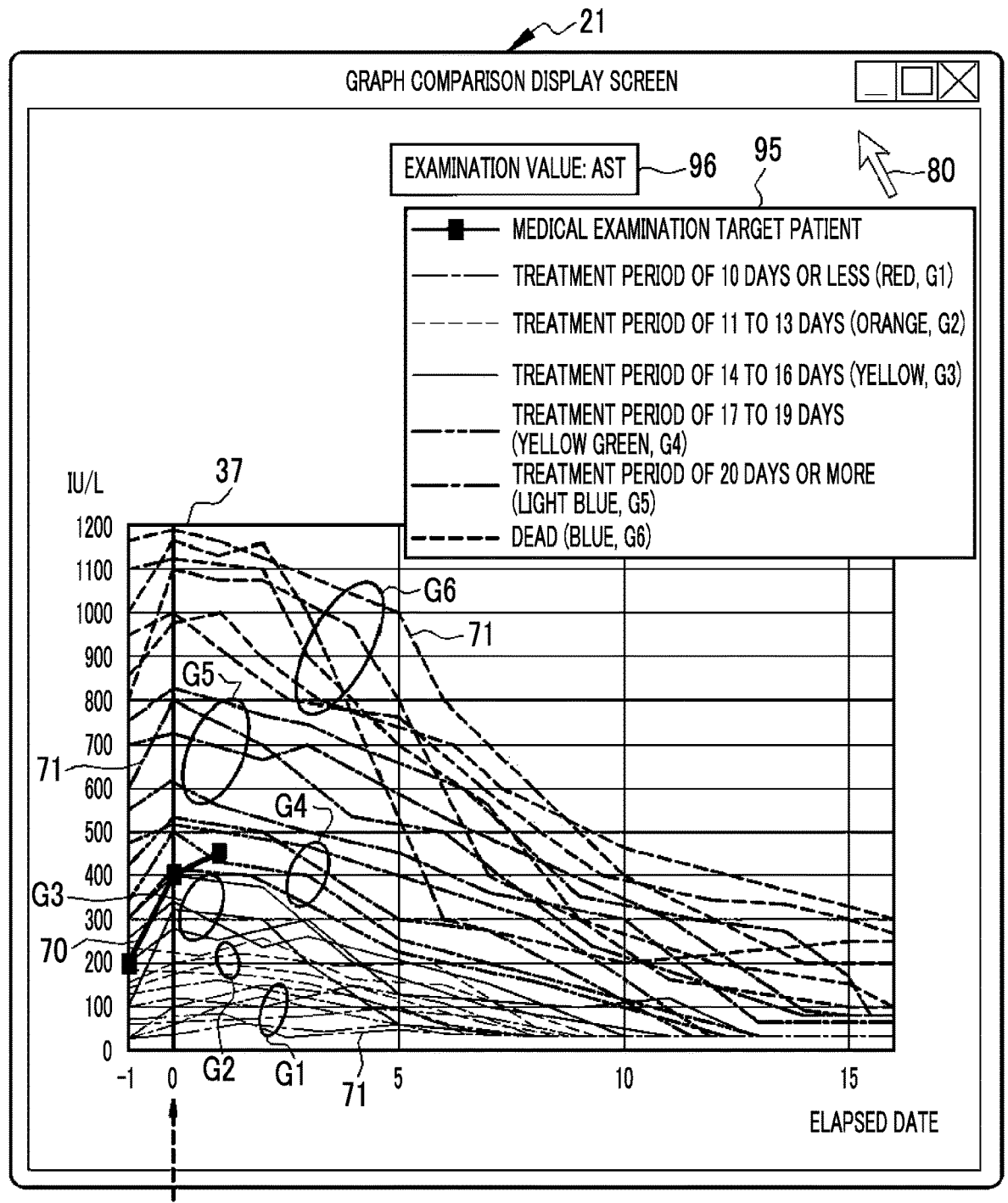
FIG. 28 is a diagram showing a graph comparison display screen in the fifth embodiment.

In this case, the administration start date of the therapeutic drug is set as the reference date by the screen display control unit 49. Therefore, in the case of displaying the graphs 70 and 71 so as to overlap each other, the graphs 70 and 71 are displayed along the time axis with the administration start date of the therapeutic drug as the elapsed date "0", as shown in FIG. 28. The same also applies to a case where the line graph 70 and the point 71A are displayed so as to overlap each other.

Comparative cases in this case are medical examination data of patients having at least the same disease name and therapeutic drug as the medical examination target patient or patients having the same type of disease name and therapeutic drug as the medical examination target patient. If disease names are the same or the same type, the items of examination values are also approximately the same between comparative cases and the medical examination data of the medical examination target patient. In addition, if therapeutic drugs are the same or the same type, the treatment effect is the same. Therefore, it is possible to acquire comparative cases that are easy to be compared with the medical examination data of the medical examination target patient.

The disease name and therapeutic drug table 130 may be recorded in the storage device 25C of the medical record DB server 12. In this case, only the disease name and the therapeutic drug of the medical examination target patient are included in the second acquisition request. The search unit 57 reads disease names and therapeutic drugs of the same type as the disease name and the therapeutic drug of the medical examination target patient from the disease name and therapeutic drug table 130, and searches for medical examination data of the electronic medical record of patients, in which the disease name and the therapeutic drug of the medical examination target patient of the second acquisition request and the disease names and the therapeutic drugs of the same type as the disease name and the therapeutic drug of the medical examination target patient read from the disease name and therapeutic drug table 130 are recorded in the medical examination and/or treatment records, as comparative cases.

The methods of acquiring comparative cases in the respective embodiments described above may be used in combination. For example, medical examination data having the same CP and surgical contents as the medical examination target patient is acquired as a comparative case. Comparative cases may also be searched for according to attributes such as patient's age, sex, and residential area. In a case where genetic test information is included in the medical examination data, genetic test information may be used to search for comparative cases. Alternatively, comparative cases may be determined according to the degree of similarity with the examination value of the medical examination target patient. The degree of similarity is calculated based on, for example, the examination value of each item of the medical examination target patient and the examination value of each item of a patient other than the medical examination target patient on the acquisition date before the reference date.

In the first embodiment described above, an example is shown in which six types of conditions are registered in the conditions and display color table and comparative cases or the rectangular region 105 are assigned to six groups and color-coded into six display colors. However, the conditions may be set more finely (for example, "treatment period of 6 to 8 days" of the conditions in the conditions and display color table 50 shown in FIG. 10 is divided into three types of conditions "treatment period of 6 days", "treatment period of 7 days", and "treatment period of 8 days"), and the number of groups and display colors for assigning the comparative cases or the rectangular regions 105 may be increased.

Examination values are not limited to the examination values of vital signs or the examination values of subject examinations exemplified in the embodiments described above. Examination values may include a measurement value indicating the feature of a lesion in an examination image, which is obtained by performing image analysis of an examination image, such as a computed tomography (CT) image, a magnetic resonance imaging (MRI) image, or a simple X-ray image. As examples of the measurement value, measurement values regarding pixel values such as the average, variance, maximum, and minimum values of pixel values in the region of a lesion, measurement values regarding the shape such as the position of the region of a lesion and the circularity of the outline of the region, and measurement values regarding the size such as the radius, area, and volume of the region of a lesion can be mentioned. In this case, on the medical examination data display screen 20, the thumbnail of the examination image may be displayed together with the graph showing the time-series change in the measurement value.

The hardware configuration of a computer, which forms the medical examination assistance server 11 corresponding to the medical examination assistance apparatus of the present invention, can be modified in various ways. For example, in order to improve the processing capacity or reliability, the medical examination assistance server 11 may be formed by a plurality of server computers that are separated from each other as hardware. Specifically, the functions of the reception unit 46 and the acquisition unit 47 and the functions of the display form determination unit 48 and the screen display control unit 49 may be distributed in two server computers. In this case, the two server computers form a medical examination assistance system. Alternatively, the medical record DB server 12 may be removed and the electronic medical record DB 14 may be provided in the medical examination assistance server 11 to integrate the medical examination assistance server 11 and the medical record DB server 12, and the CPU 27B of the medical examination assistance server 11 may have the function of the search unit 57.

In the first embodiment described above, the case has been exemplified in which the medical examination assistance server 11 generates the display screens 20 and 21 and the display screens 20 and 21 are reproduced on the client terminal 10 side based on the XML data of the display screens 20 and 21 from the medical examination assistance server 11 and are displayed on the display 29A. However, the medical examination data of the medical examination target patient as a generation source of the display screens 20 and 21, comparative cases, and display color designation information may be transmitted from the medical examination assistance server 11 to the client terminal 10, and the display screens 20 and 21 may be generated on the client terminal 10 side. In this case, the screen display control unit 49 is constructed in the CPU 27A of the client terminal 10. In this case, the client terminal 10 and the medical examination assistance server 11 form a medical examination assistance system.

Each of the functional units 46 to 49 may be constructed in the CPU 27A of the client terminal 10, and the client terminal 10 may be operated as a medical examination assistance apparatus. In this case, the reception unit 46 receives various distribution instructions from the GUI control unit 35. In addition, the screen display control unit 49 outputs the generated display screens 20 and 21 to the GUI control unit 35.

Thus, the hardware configuration of a computer can be appropriately changed according to the required performance, such as processing capacity, safety, or reliability. Needless to say, in order to ensure the safety or reliability, an application program, such as the medical examination assistance program 45 and the DB program 55, may be duplicated or may be stored in a plurality of storage devices in a distributed manner, without being limited to hardware.

In each of the embodiments described above, the medical examination assistance system 2 constructed in one medical facility is exemplified, and the medical examination assistance server 11 is used in one medical facility. However, the medical examination assistance server 11 may be configured to be usable in a plurality of medical facilities.

In each of the embodiments described above, the medical examination assistance server 11 is communicably connected to the client terminal 10, which is installed in one medical facility, through the network 13, such as a LAN, and provides various functions corresponding to various requests from the client terminal 10. In order to make the medical examination assistance server 12 available in a plurality of medical facilities, the medical examination assistance server 12 is communicably connected to each of the client terminals 10 installed in the plurality of medical facilities, for example, through a wide area network (WAN), such as the Internet or a public communication network. Then, the medical examination assistance server 11 receives requests from the client terminals 10 in the plurality of medical facilities through the WAN, and provides various functions to each client terminal 10. In the case of using a WAN, it is preferable to construct a virtual private network (VPN) or to use a communication protocol with a high security level, such as hypertext transfer protocol secure (HTTPS), in consideration of information security.

In this case, the installation location and management entity of the medical examination assistance server 11 may be a data center managed by a company that is different from the medical facilities, or may be one of the plurality of medical facilities, for example.

In each of the embodiments described above, an example is shown in which display colors are exemplified as a display form determined by the display form determination unit 48 and a plurality of line graphs 71 or a heat map is color-coded and displayed with display colors determined according to the treatment outcome. However, the present invention is not limited thereto. Instead of or in addition to the display colors, various textures, such as the types of line segments, the types of points, and a filling method, may be changed according to the treatment outcome, so that the degree of good or poor treatment outcome of each comparative case is visually displayed. For example, in FIG. 15, even if the display color of the line graph 71 is unified in red, it is possible to recognize the degree of good or poor treatment outcome of each comparative case by using different types of line segments. In FIG. 22, even if the display color of each rectangular region 105 is unified in red, it is possible to compare the symptoms of the medical examination target patient and comparative cases by making the method of filling each rectangular region 105 different as shown by hatching. However, a display method based on color-coding with display colors is preferable due to easiness in terms of observation.

In the present invention, it is also possible to appropriately combine the above-described various embodiments or various modification examples. Without being limited to the embodiments described above, it is needless to say that various configurations can be adopted without departing from the scope of the present invention. In addition to the program, the invention also extends to a storage medium that stores the program.

EXPLANATION OF REFERENCES

2: medical examination assistance system
10: client terminal
11: medical examination assistance server (medical examination assistance apparatus)
14: electronic medical record DB (case database)
21: graph comparison display screen
27: CPU
37: graph display region (two-dimensional region)
45: medical examination assistance program (operation program)
47: acquisition unit
48: display form determination unit
49: screen display control unit
50, 100: conditions and display color table
57: search unit
66, 102, 111: display color designation information
70: line graph (medical examination target patient graph)
71: line graph (comparative case result information, comparative case graph)
71A: point (comparative case result information, comparative case graph)
105: rectangular region
115: heat map (comparative case result information)
128: isoplethic curve

What is claimed is:

1. A medical examination assistance apparatus, comprising:
a processor, configured to:
acquire, from a case database in which medical examination data including examination values registered in time series is registered for each patient, the medical examination data of a medical examination target patient and a plurality of comparative cases that are the medical examination data of comparison targets;
assign the plurality of comparative cases to a plurality of groups comprising a first group and a second group on the basis of a treatment outcome of each of the comparative cases, wherein the treatment outcome is determined according to a length of a treatment period of each of the comparative cases or the number of variance occurrence of each of the comparative cases, wherein the treatment outcome of at least one of first comparative cases assigned to the first group is less than a first value, and the treatment outcome of at least one of second comparative cases assigned to the second group is equal to or greater than the first value;

determine a display form among a plurality of display forms comprising a first display form and a second display form for each of the plurality of comparative cases according to the treatment outcome of each of the plurality of comparative cases, wherein the first display form is determined for the at least one of first comparative cases for the first group, the second display form is determined for the at least one of second comparative cases for the second group, and the first display form is different from the second display form;

generate comparative case result information indicating the treatment outcome of each of the plurality of comparative cases according to the display form of each of the plurality of comparative cases, wherein the comparative case result information comprises first comparative case result information indicating the treatment outcome of at least one of the first comparative cases generated according to the first display form, and second comparative case result information indicating the treatment outcome of at least one of the second comparative cases generated according to the second display form; and perform control to display a medical examination target patient graph showing a time-series change in each of the examination values of the medical examination target patient and the comparative case result information comprising the first comparative case result information and the second comparative case result information on a display screen so as to overlap each other.

2. The medical examination assistance apparatus according to claim 1, wherein the processor is configured to generate a comparative case graph showing a time-series change in the examination value of each of the comparative cases, as the comparative case result information, for each of the comparative cases, and distinguishes the plurality of comparative case graphs according to the display form.

3. The medical examination assistance apparatus according to claim 2, wherein the comparative case graph is shown by a line graph connecting the examination values of each of the comparative cases to each other using lines for each acquisition date of the examination value.

4. The medical examination assistance apparatus according to claim 2, wherein the comparative case graph is shown by points obtained by plotting the examination values of each of the comparative cases for each acquisition date of the examination value.

5. The medical examination assistance apparatus according to claim 2, wherein a reference date for displaying the medical examination target patient graph and the comparative case graph so as to overlap each other is set along a time axis.

6. A medical examination assistance apparatus comprising:

a processor configured to:

acquire, from a case database in which medical examination data comprising examination values registered in time series is registered for each patient, the medical examination data of a medical examination target patient and a plurality of comparative cases that are the medical examination data of comparison targets;

set a plurality of rectangular regions including first rectangular region and second rectangular region by dividing a two-dimensional region having two axes of the examination value and an acquisition date of the examination value in units of the examination value and units of the acquisition date, assign the plurality of comparative cases to a plurality of groups comprising a first group and a second group, wherein the examination value of at least one of first comparative cases assigned to the first group is present within the first rectangular region, and the examination value of at least one of second comparative cases is present within the second rectangular region;

determine a display form among a plurality of display forms comprising a first display form and a second display form for each of the plurality of groups on the basis of an index value according to a treatment outcome of a comparative case assigned to each of the plurality of groups, wherein the treatment outcome is determined according to a length of a treatment period of each of the comparative cases or the number of variance occurrence of each of the comparative cases, wherein the first display form is determined on the basis of a first index value according to a treatment outcome of the at least one first comparative cases for the first group, the second display form is determined on the basis of a second index value according to a treatment outcome of the at least one second comparative cases for the second group, wherein the first index value is less than a first value, and the second index value is equal to or greater than the first value;

generate a heat map, in which the rectangular regions are distinguished according to the display form of each of the plurality group, wherein the first rectangular region is generated according to the first display form, and wherein the second rectangular region is generated according to the second display form; and perform control to display a medical examination target patient graph showing a time-series change in each of the examination values of the medical examination target patient and the heat map so as to overlap each other.

7. The medical examination assistance apparatus according to claim 6, wherein the index value is an average value of the treatment outcomes.

8. The medical examination assistance apparatus according to claim 6, wherein the index value is a ratio between the number of comparative cases with good treatment outcomes and the number of comparative cases with poor treatment outcomes.

9. The medical examination assistance apparatus according to claim 1, wherein the medical examination data includes a clinical path that summarizes a treatment plan for a patient, and the comparative cases are the medical examination data having the same clinical path as the medical examination target patient.

10. The medical examination assistance apparatus according to claim 5,
wherein the medical examination data includes a clinical path that summarizes a treatment plan for a patient,
the comparative cases are the medical examination data having the same clinical path as the medical examination target patient, and
wherein an application start date of the clinical path is set as the reference date.

11. The medical examination assistance apparatus according to claim 1,
wherein the medical examination data includes contents of surgery performed on a patient, and the comparative cases are the medical examination data having the same surgical contents as the medical examination target patient.

12. The medical examination assistance apparatus according to claim 5,
wherein the medical examination data includes contents of surgery performed on a patient, and the comparative cases are the medical examination data having the same surgical contents as the medical examination target patient, and
wherein a date of the surgery is set as the reference date.

13. The medical examination assistance apparatus according to claim 1,
wherein the medical examination data includes a disease name of a patient and a therapeutic drug administered to the patient, and
the comparative cases are the medical examination data having the same disease name and therapeutic drug as the medical examination target patient.

14. The medical examination assistance apparatus according to claim 5,
wherein the medical examination data includes a disease name of a patient and a therapeutic drug administered to the patient,
the comparative cases are the medical examination data having the same disease name and therapeutic drug as the medical examination target patient, and
wherein an administration start date of the therapeutic drug is set as the reference date.

15. The medical examination assistance apparatus according to claim 1,
wherein the processor is configured to assign the plurality of comparative cases to the plurality of groups on the basis of the treatment outcome according to the length of a treatment period and whether each of the comparative cases is alive or dead.

16. The medical examination assistance apparatus according to claim 1,
wherein the medical examination data includes a clinical path that summarizes a treatment plan for each patient and the variance that does not conform to the treatment plan, and
the processor is configured to assign the plurality of comparative cases to a plurality of groups on the basis of the treatment outcome according to the number of the variance occurrence.

17. The medical examination assistance apparatus according to claim 1,
wherein the display forms are display colors.

18. An operation method of a medical examination assistance apparatus, comprising:
acquiring, from a case database in which medical examination data including examination values registered in time series is registered for each patient, the medical examination data of a medical examination target patient and a plurality of comparative cases that are the medical examination data of comparison targets;
assigning the plurality of comparative cases to a plurality of groups comprising a first group and a second group on the basis of a treatment outcome of each of the comparative cases, wherein the treatment outcome is determined according to a length of a treatment period of each of the comparative cases or the number of variance occurrence of each of the comparative cases, wherein the treatment outcome of at least one of first comparative cases assigned to the first group is less than a first value, and the treatment outcome of at least one of second comparative cases assigned to the second group is equal to or greater than the first value;
determining a display form among a plurality of display forms comprising a first display form and a second display form for each of the plurality of comparative cases according to the treatment outcome of each of the plurality of comparative cases, wherein the first display form is determined for the at least one of first comparative cases for the first group, the second display form is determined for the at least one of second comparative cases for the second group, and the first display form is different from the second display form;
generating comparative case result information indicating the treatment outcome of each of the plurality of comparative cases according to the display form of each of the plurality of comparative cases, wherein the comparative case result information comprises first comparative case result information indicating the treatment outcome of at least one of the first comparative cases generated according to the first display form, and second comparative case result information indicating the treatment outcome of at least one of the second comparative cases generated according to the second display form;
and
performing control to display a medical examination target patient graph showing a time-series change in each of the examination values of the medical examination target patient and the comparative case result information comprising the first comparative case result information and the second comparative case result information on a display screen so as to overlap each other.

19. A non-transitory computer readable recording medium storing an operation program of a medical examination assistance apparatus, causing a computer to:
acquire, from a case database in which medical examination data including examination values registered in time series is registered for each patient, the medical examination data of a medical examination target patient and a plurality of comparative cases that are the medical examination data of comparison targets;
assign the plurality of comparative cases to a plurality of groups comprising a first group and a second group on the basis of a treatment outcome of each of the comparative cases, wherein the treatment outcome is determined according to a length of a treatment period of each of the comparative cases or the number of variance occurrence of each of the comparative cases, wherein the treatment outcome of at least one of first comparative cases assigned to the first group is less than a first value, and the treatment outcome of at least one of second comparative cases assigned to the second group is equal to or greater than the first value;

determine a display form among a plurality of display forms comprising a first display form and a second display form for each of the plurality of comparative cases according to the treatment outcome of each of the plurality of comparative cases, wherein the first display form is determined for the at least one of first comparative cases for the first group, the second display form is determined for the at least one of second comparative cases for the second group, and the first display form is different from the second display form;

generate comparative case result information indicating the treatment outcome of each of the plurality of comparative cases according to the display form of each of the plurality of comparative cases, wherein the comparative case result information comprises first comparative case result information indicating the treatment outcome of at least one of the first comparative cases generated according to the first display form, and second comparative case result information indicating the treatment outcome of at least one of the second comparative cases generated according to the second display form; and perform control to display a medical examination target patient graph showing a time-series change in each of the examination values of the medical examination target patient and the comparative case result information comprising the first comparative case result information and the second comparative case result information on a display screen so as to overlap each other.

20. A medical examination assistance system comprising a medical examination assistance apparatus, comprising:

a processor, configured to:

acquire, from a case database in which medical examination data including examination values registered in time series is registered for each patient, the medical examination data of a medical examination target patient and a plurality of comparative cases that are the medical examination data of comparison targets;

assign the plurality of comparative cases to a plurality of groups comprising a first group and a second group on the basis of a treatment outcome of each of the comparative cases, wherein the treatment outcome is determined according to a length of a treatment period of each of the comparative cases or the number of variance occurrence of each of the comparative cases, wherein the treatment outcome of at least one of first comparative cases assigned to the first group is less than a first value, and the treatment outcome of at least one of second comparative cases assigned to the second group is equal to or greater than the first value;

determine a display form, among a plurality of display forms comprising a first display form and a second display form for each of the plurality of comparative cases according to the treatment outcome of each of the plurality of comparative cases, wherein the first display form is determined for the at least one of first comparative cases for the first group, the second display form is determined for the at least one of second comparative cases for the second group, and the first display form is different from the second display form;

generate comparative case result information indicating the treatment outcome of each of the plurality of comparative cases according to the display form of each of the plurality of comparative cases, wherein the comparative case result information comprises first comparative case result information indicating the treatment outcome of at least one of the first comparative cases generated according to the first display form, and second comparative case result information indicating the treatment outcome of at least one of the second comparative cases generated according to the second display form; and perform control to display a medical examination target patient graph showing a time-series change in each of the examination values of the medical examination target patient and the comparative case result information comprising the first comparative case result information and the second comparative case result information on a display screen so as to overlap each other.

21. The medical examination assistance apparatus according to claim 1, wherein the processor is further configured to:

determine whether to continue a current treatment or switch to another treatment for the medical examination target patient by comparing the time series change thereof and the comparative cases.

22. The medical examination assistance apparatus according to claim 1, wherein the processor is further configured to:

predict a transition of the examination values of the medical examination target patient and determine a next visit date of the medical examination target patient.

* * * * *